US008569033B2

(12) United States Patent
Watanabe et al.

(10) Patent No.: US 8,569,033 B2
(45) Date of Patent: Oct. 29, 2013

(54) SURFACTANT TOLERANT CELLULASE AND METHOD FOR MODIFICATION THEREOF

(75) Inventors: Manabu Watanabe, Odawara (JP); Koji Yanai, Odawara (JP); Yumiko Tsuyuki, Odawara (JP)

(73) Assignee: Meiji Seika Pharma Co., Ltd., Tokyo (JP)

( * ) Notice: Subject to any disclaimer, the term of this patent is extended or adjusted under 35 U.S.C. 154(b) by 1898 days.

(21) Appl. No.: 10/582,002

(22) PCT Filed: Dec. 7, 2004

(86) PCT No.: PCT/JP2004/018184
§ 371 (c)(1),
(2), (4) Date: Jun. 7, 2006

(87) PCT Pub. No.: WO2005/056787
PCT Pub. Date: Jun. 23, 2005

(65) Prior Publication Data
US 2007/0099265 A1  May 3, 2007

(30) Foreign Application Priority Data

Dec. 8, 2003 (JP) ................................. 2003-409692

(51) Int. Cl.
*C12N 9/42* (2006.01)
*C12N 9/26* (2006.01)
*C12N 1/00* (2006.01)
*C12N 15/00* (2006.01)
*C12P 21/06* (2006.01)
*C07H 21/04* (2006.01)

(52) U.S. Cl.
USPC ....... 435/209; 435/69.1; 435/201; 435/254.1; 435/320.1; 536/23.2

(58) Field of Classification Search
None
See application file for complete search history.

(56) References Cited

U.S. PATENT DOCUMENTS

| 5,792,641 | A | 8/1998 | Schuelein et al. |
| 5,948,672 | A | 9/1999 | Rasmussen et al. |
| 6,114,296 | A | 9/2000 | Schuelein et al. |
| 6,159,720 | A | 12/2000 | Murashima et al. |
| 6,270,968 | B1 | 8/2001 | Dalbøge et al. |
| 6,277,596 | B1 | 8/2001 | Watanabe et al. |
| 6,403,362 | B1 | 6/2002 | Moriya et al. |
| 6,921,655 | B1 | 7/2005 | Nakamura et al. |
| 2001/0036910 | A1 | 11/2001 | Rasmussen et al. |
| 2003/0119167 | A1 | 6/2003 | Rasmussen et al. |
| 2005/0143275 | A1 | 6/2005 | Murashima et al. |

FOREIGN PATENT DOCUMENTS

| CN | 1230988 A | 10/1999 |
| WO | WO 91/17243 A | 11/1991 |
| WO | WO 94/07998 A | 4/1994 |
| WO | WO 97/43409 A | 11/1997 |
| WO | WO 98/03667 A | 1/1998 |
| WO | WO 98/11239 A | 3/1998 |
| WO | WO 00/24879 A1 | 5/2000 |
| WO | WO 01/90375 A1 | 11/2001 |

OTHER PUBLICATIONS

Whisstock et al. Quaterly Reviews of Biophysics, 2003, "Prediction of protein function from protein sequence and structure", 36(3): 307-340.*
Branden et al. Introduction to protein structure, Gerald Publishing Inc., New York, p. 247, 1991.*
Witkowski et al. Conversion of a beta-ketoacyl synthase to a malonyl decarboxylase by replacement of the active-site cysteine with glutamine, Biochemistry. Sep. 7, 1999;38(36):11643-50.*
Guo et al. Protein tolerance to random amino acid change, Proc Natl Acad Sci U S A. Jun. 22, 2004;101(25):9205-10. Epub Jun. 14, 2004.*
B. Henrissat, et al, "Updating the Sequence-Based Classification of Glycosyl Hydrolases", Biochemical Journal, vol. 316, 1996, pp. 695-696.
Daniel E. Otzen, et al, "A Comparative Study of the Unfolding of the Endoglucanase Cel45 From *Humicola insolens* in Denaturant and Surfactant", Protein Science, vol. 8, 1999, pp. 1878-1887.
Iori Maeda, et al, "Purification and Characterization of a Cellulase From the Giant Snail *Achatina fulica*", Biosci. Biotechnol. Biochem., vol. 60, No. 1, 1996, pp. 122-124.
Elizabeth J. Waters, et al, "Sequence Analysis of Grape (*Vitis vinifera*) Berry Chitinases That Cause Haze Formation in Wines", J. Agric. Food Chem, vol. 46, 1998, pp. 4950-4957.
Klaus Klarskov, et al, "Cellobiohydrolase I From *Trichoderma reesei*: Identification of an Active-Site Nucleophile and Additional Information on Sequence Including the Glycosylation Pattern of the Core Protein", Carbohydrate Research, vol. 304, No. 2, 1997, pp. 143-154.
F. P. M. O'Harte, et al, "Improved Stability, Insulin-Releasing Activity and Antidiabetic Potential of Two Novel N-Terminal Analogues of Gastric Inhibitory Polypeptide: N-acetyl-GIP and pGlu-GIP", Diabetologia, vol. 45, 2002, pp. 1281-1291.
Y. Odagaki, et al, "The Crystal Structure of Pyroglutamyl Peptidase I From *Bacillus amyloliquefaciens* Reveals a New Structure for a Cysteine Protease", Structure Fold Des., vol. 7, No. 4, 1999, pp. 399-411.
Kleywegt G. J. et al, "The crystal structure of the catalytic core domain of endoglucanase I from *Trichoderma reesei* at 3.6 A resolution, and a comparison with related enzymes", Journal of Molecular Biology, London, GB, vol. 272, No. 3, Sep. 26, 1997, pp. 383-397, XP004461458.

* cited by examiner

Primary Examiner — Robert Mondesi
Assistant Examiner — Iqbal H Chowdhury
(74) *Attorney, Agent, or Firm* — Sughrue Mion, PLLC

(57) ABSTRACT

A method for suppressing a reduction in an endoglucanase activity in the presence of a surfactant, characterized by modifying a protein having the endoglucanase activity in which the N-terminus is an amino acid other than pyroglutamic acid, to a protein having the N-terminus of pyroglutamic acid, is disclosed. Further, a modified protein having an endoglucanase activity wherein the N-terminal amino acid is converted into pyroglutamic acid by an amino acid modification, a polynucleotide encoding the protein, an expression vector comprising the polynucleotide, a host cell transformed with the expression vector, and a process for producing the protein by cultivating the host cell, are disclosed.

8 Claims, 2 Drawing Sheets

Figure 1

```
NCE4    MRSSPLLRSAVVAALPVLAL----------AADGKSTRYWDCCKPSCGWAK       21
                ************** *
STCE1   MRSSPVLRTALAAALPLAALA---------ADGKSTRYWDCCKPSCSWPG        20
                 *  ***********  ***
NCE5    MQLPLTTLLTLLPALAA------------AQSGSGRTTRYWDCCKPSCAWPG       23
         Signal peptide →         Catalytic domain    →

NCE4    KAPVNQPVFSCNANFQRLTDF-DAKSGCEPGGVAYSCADQTPWAVNDDFA         70
        ** ****** * *****    ****  ** ** *********** *
STCE1   KASVNQPVFACSANFQRISDP-NVKSGCD-GGSAYACADQTPWAVNDNFS         68
          *    **  *       * *  ****  **  ** * **  **** *
NCE5    KGPA---PVRTCDRWDNPLFDGGNTRSGCDAGGGAYMCSDQSPWAVSDDLA-       71

NCE4    FGFAATSIAGSNEAGWCCACYELTFTSGPVAGKKMVVQSTSTGGDLGSNH         120
        ******* * *** *** ************* ************* **
STCE1   YGFAATSISGGNEASWCCGCYELTFTSGPVAGKTMVVQSTSTGGDLGTNH         118
        ** **   *  ** ***  ************  * **   ******  **
NCE5    YGWAAVNIAGSNERQWCCACYELTFTSGPVAGKRMIVQASNTGGDLGNNH         121

NCE4    FDLNIPGGGVGIFDGCTPQFGGLP--GQRYGGISSRNECDRFPDALKPG          167
        ***  ************* *****   *  ****  *** ** *  *****
STCE1   FDLAMPGGGVGIFDGCSPQFGGLA--GDRYGGVSSRSQCDSFPAALKPG          165
         **  **********   *  * *        *  *** * *  **  ****
NCE5    FDIAMPGGGVGIFNACTDQYGAPPNGWGQRYGGISQRHECDAFPEKLKPG         171
```

Figure 2

```
NCE4    CYWRFDWFKNADNPSFSFRQVQCPAELVARTGCRRNDDGNFPAVQIPSSS        217
        ************** * ****** ******************  **
STCE1   CYWRFDWFKNADNPTFTFRQVQCPSELVARTGCRRNDDGNFPVFTPPSGG        215
        ******** *****   *** ** * **  ** *
NCE5    CYWRFDWFLNADNPSVNWRQVSCPAEIVAKSGCSR-------------          206
                                                 Linker→

NCE4    TSSPVGQPTSTSTTSTSTTSSPPVQPTTPS--------GCTAERWA            255
        **    * ****     * *         ** * ***
STCE1   QSSSSSSSSSSAKPTSTSTSTTSTKATSTTSTASSQTSSSTGGGCAAQRWA      265

NCE5    ---------------------------------------------
                                                 CBD→

NCE4    CQCGGNGWSGCTTCVAGSTCTKINDWYHQCL        286
        ***** * ******** * ** * ********
STCE1   CQCGGIGFSGCTTCVSGTTCNKQNDWYSQCL        295

NCE5    ---------------------------------
```

SURFACTANT TOLERANT CELLULASE AND METHOD FOR MODIFICATION THEREOF

TECHNICAL FIELD

The present invention relates to a method for modifying the N-terminus of a protein having an endoglucanase activity (particularly, cellulase belonging to family 45 and having an endoglucanase activity) to pyroglutamic acid, to convert the protein into cellulase having an endoglucanase activity whose reduction in the presence of a surfactant is small, and relates to the cellulase.

BACKGROUND ART

Cellulose biomass is said to be the most abundant resource in natural resources, and thus an efficient application of cellulase systems which decompose the cellulose biomass is desired in various fields. In this development process, various cellulases were purified and characterized, and further, various cellulase genes were cloned, and classified into families by analyzing the sequence homology (see non-patent reference 1).

In another aspect, cellulases are utilized, based on their properties, in various industrial fields, particularly the field of fabric processing. For example, treatment with cellulase is carried out to improve the touch and/or appearance of cellulose-containing fabric, or for a "biowash", which imparts a "stonewash" appearance to colored cellulose-containing fabric, thereby providing the fabric with localized color variations. Further, in the process for manufacturing lyocell, cellulase is used for removing the fuzz generated in the process from the fabric surface. In this connection, lyocell is a regenerated cellulose fabric derived from wood pulp, and has recently attracted attention for its properties (such as high strength or water absorption) and as a production process that causes less environmental pollution.

Hitherto, it has been considered that cellulase decomposes cellulose by the collaborative effect of plural enzymes, i.e., synergy effect. The cellulase group consisting of plural enzymes contains enzymes having properties inappropriate for the field of fabric processing (such as an enzyme which lowers a fiber strength). Therefore, an attempt to separate enzyme components appropriate for fabric processing from the cellulase group, and to produce the enzyme components, has been carried out by utilizing protein separation techniques and/or genetic engineering techniques. Particularly, cellulases derived from microorganisms belonging to filamentous fungi such as genus *Trichoderma* or genus *Humicola* have been subjected to serious study. For example, as cellulase components, CBH I, EG V (see patent reference 1), NCE2, NCE4, and NCE5 in genus *Humicola*, and CBH I, CBH II, EG II, and EG III in genus *Trichoderma* were isolated, and thus, cellulase preparations containing as the major components one or more specific cellulase components appropriate for each purpose can be produced by preparing overexpressed enzymes or monocomponent enzymes using genetic engineering techniques. Further, it is clarified that cellulases belonging to family 45, such as NCE4 (see patent reference 2), NCE5 (see patent reference 3), RCE1 (see patent reference 4), or STCE1 (see International Application No. PCT/JP2004/15733), are very useful in the above fields.

In still another aspect, when cellulases are used as a detergent for clothing, not only quantitative improvement of cellulase components used but also qualitative one is desired. More particularly, a detergent for clothing contains various surfactants, and a solution obtained by solubilizing the detergent for clothing in water is alkaline (pH10 to pH11). Therefore, it is necessary that cellulases contained in a detergent for clothing should be resistant to various surfactants under alkaline conditions. As a report in which a reduction in an activity in the presence of a surfactant is suppressed, it was reported by Otzen, D. E. et al. that when a mutation was introduced into the internal amino acid sequence of Cel45 derived from *Humicola insolens*, the activity thereof at pH7 in the presence of linear alkyl benzene sulfonate (LAS) was approximately 3.3 times higher than that of the wild-type (see non-patent reference 2). However, it is found that the suppression of a reduction in the activity in the presence of the surfactant, provided by the mutation, is limited to Cel45 or homologous proteins thereof, and that is not applicable to endoglucanases belonging to family 45 having a low homology with Cel45.

(patent reference 1) International Publication WO91/17243
(patent reference 2) International Publication WO98/03667
(patent reference 3) International Publication WO01/90375
(patent reference 4) International Publication WO00/24879
(non-patent reference 1) Henrissat B., Bairoch A. Updating the sequence-based classification of glycosyl hydrolases. Biochem. J. 316:695-696 (1996)
(non-patent reference 2) Daniel E. Otzen, Lars Christiansen, Martin Schulein. A comparative study of the unfolding of the endoglucanase Cel45 from *Humicola insolens* in denaturant and surfactant. Protein Sci. 8:1878-1887 (1999)

DISCLOSURE OF INVENTION

Problems to be Solved by the Invention

An object of the present invention is to provide a method for converting a protein having an endoglucanase activity (particularly, a protein belonging to family 45 and having an endoglucanase activity) to a protein having an endoglucanase activity whose reduction in the presence of a surfactant is small; a vector used in the method; a protein having an endoglucanase activity whose reduction in the presence of a surfactant is small; and a polynucleotide encoding the same. A further object of the present invention is to provide, using the above, a microorganism which efficiently produces a useful protein as an enzyme for the washing of clothing.

Means for Solving the Problems

The present inventors conducted intensive studies, and as a result, found that proteins in which pyroglutamic acid (hereinafter sometimes referred to as pQ) or a peptide containing pQ was added to the N-terminus of each protein belonging to family 45 and having an endoglucanase, i.e., N-terminus-added cellulases, had an endoglucanase activity exhibiting no significant reduction in the activity in the presence of a surfactant, in comparison with wild-type cellulases.

The feature that a high endoglucanase activity is maintained in the presence of an anionic surfactant is particularly useful as enzymes for the washing of clothing, but such a cellulase is not known. Further, it has not been reported that functions inherent in an enzyme can be maintained in the presence of a surfactant by adding thereto pyroglutamic acid or a peptide containing the same.

In another aspect of the present invention, with respect to all cellulases in which the N-terminal amino acid is not protected and the maintenance of the activity in the presence of a surfactant is desired, it is possible, by adding pyroglutamic acid or a peptide containing the same to the cellulase, to suppress a reduction in the activity in the presence of a surfactant. The cellulase which pyroglutamic acid or a peptide containing the same are added is not particularly limited, but cellulases belonging to family 45 are preferable.

Accordingly, the present invention includes the following:
(1) a method for suppressing a reduction in an endoglucanase activity in the presence of a surfactant, characterized by modifying a protein having the endoglucanase activity in which the N-terminus is an amino acid other than pyroglutamic acid, to a protein having the N-terminus of pyroglutamic acid;
(2) the method of (1), wherein the modification is carried out by adding pyroglutamic acid or an amino acid convertible into pyroglutamic acid, or a peptide having the N-terminus of pyroglutamic acid or an amino acid convertible into pyroglutamic acid, to the N-terminus of the protein having the endoglucanase activity in which the N-terminus is an amino acid other than pyroglutamic acid;
(3) the method of (1), wherein the modification is carried out by substituting pyroglutamic acid or an amino acid convertible into pyroglutamic acid, or a peptide having the N-terminus of pyroglutamic acid or an amino acid convertible into pyroglutamic acid, for the N-terminal amino acid or an N-terminal region of the protein having the endoglucanase activity in which the N-terminus is an amino acid other than pyroglutamic acid;
(4) the method of any one of (1) to (3), wherein the protein having the endoglucanase activity in which the N-terminus is an amino acid other than pyroglutamic acid is a cellulase belonging to family 45;
(5) a modified protein having an endoglucanase activity wherein the N-terminal amino acid is converted into pyroglutamic acid by an amino acid modification;
(6) the modified protein of (5), which is obtainable by the method of any one of (1) to (4);
(7) a protein selected from the group consisting of:
(a) a protein comprising the amino acid sequence of SEQ ID NO: 2, 4, 38, or 40;
(b) a modified protein comprising an amino acid sequence in which one or plural amino acids are deleted, substituted, inserted, or added in the amino acid sequence of SEQ ID NO: 2, 4, 38, or 40, and having an endoglucanase activity whose reduction in the presence of a surfactant is small; and
(c) a homologous protein comprising an amino acid sequence having at least 85% homology with a protein comprising the amino acid sequence of SEQ ID NO: 2, 4, 38, or 40, and having an endoglucanase activity whose reduction in the presence of a surfactant is small;
(8) a polynucleotide encoding the protein of any one of (5) to (7);
(9) a polynucleotide selected from the group consisting of:
(a) a polynucleotide comprising the nucleotide sequence of SEQ ID NO: 1, 3, 37, or 39;
(b) a polynucleotide comprising a nucleotide sequence in which one or plural nucleotides are deleted, substituted, inserted, or added in the nucleotide sequence of SEQ ID NO: 1, 3, 37, or 39, and encoding a protein having an endoglucanase activity whose reduction in the presence of a surfactant is small; and
(c) a polynucleotide hybridizing under stringent conditions to a polynucleotide consisting of the nucleotide sequence of SEQ ID NO: 1, 3, 37, or 39, and encoding a protein having an endoglucanase activity whose reduction in the presence of a surfactant is small;
(10) an expression vector comprising the polynucleotide of (8) or (9);
(11) a host cell transformed with the expression vector of (10);
(12) the host cell of (11), wherein the host cell is a yeast or filamentous fungus;
(13) the host cell of (12), the filamentous fungus is a microorganism belonging to genus *Humicola* or *Trichoderma*;
(14) the host cell of (13), the filamentous fungus is *Humicola insolens* or *Trichoderma viride*;
(15) a process for producing the protein of any one of (5) to (7), comprising:
cultivating the host cell of any one of (11) to (14), and recovering the protein from the host cell or culture obtained by the cultivation; and
(16) a protein produced by the process of (15).

Effects of the Invention

According to the present invention, it is possible to efficiently produce a novel cellulase which is useful as an enzyme for the washing of clothing and has an endoglucanase activity whose reduction in the presence of a surfactant is small.

BEST MODE FOR CARRYING OUT THE INVENTION

Protein Belonging to Family 45 and Having Endoglucanase Activity (Hereinafter Sometimes Referred to as "Cellulase Belonging to Family 45") Family 45

The term "family 45" as used herein means a protein classified into family 45 in accordance with the hydrophobic cluster analysis of carbohydrate activating enzymes by B. Henrissat and A. Bairoch {Henrissat B., Bairoch A. Updating the sequence-based classification of glycosyl hydrolases. Biochem. J. 316: 695-696 (1996)}.
Protein Having Endoglucanase Activity The term "protein having an endoglucanase activity" as used herein means an enzyme exhibiting an endoglucanase activity, i.e., endo-1,4-β-glucanase (EC3.2.1.4), which hydrolyzes the β-1,4-glucopyranosyl bond in β-1,4-glucan.
Surfactant The term "surfactant" as used herein is a detergent component contained in a detergent for clothing, and broadly classified into anionic, cationic, and nonionic surfactants. Anionic surfactants are commonly used. As preferable anionic surfactants used in the present invention, there may be mentioned, for example, linear alkyl benzene sulfonate (hereinafter sometimes referred to as LAS).
Endoglucanase Activity The term "endoglucanase activity (hereinafter referred to as "EGU")" as used herein is defined as an enzyme activity obtained by measuring a decrease in the viscosity of a carboxymethylcellulose solution in accordance with the following procedure.

As a substrate solution, carboxymethylcellulose (Hercules) was dissolved in a 0.1 mol/L Tris-HCl buffer (pH10.0) (final concentration=3.5%). To the substrate solution (5 mL) previously heated at 40° C. for 10 minutes, 0.15 mL of an enzyme solution was added, and then the whole was mixed well to carry out the reaction at 40° C. for 30 minutes. The viscosity of the reaction mixture was measured by an R type viscometer (RE100; TOKI SANGYO CO., LTD.) at 40° C. The "1 unit" of the enzyme activity is defined as an amount of enzyme which lowers the initial viscosity to ½, in each reaction condition. As an anionic surfactant, linear alkyl benzene sulfonate (Wako Pure Chemical Industries, Co., Ltd.) was used, and added to the carboxymethylcellulose solution to a final concentration of 800 ppm.

Suppression of Reduction in Endoglucanase Activity in the Presence of Surfactant "Having an endoglucanase activity whose reduction in the presence of a surfactant is small" as used herein means that, when the protein in which the N-terminus thereof is modified (N-terminus-modification-type protein) according to the present invention is compared to the original protein before performing the modification (hereinafter simply referred to as the original protein) with respect to the endoglucanase activity in the presence of the surfactant, the endoglucanase activity of the N-terminus-modification-type protein is higher than that of the original protein.

Original Protein

The original protein which may be applied to the method of the present invention is not particularly limited, so long as it is a protein having an endoglucanase activity in which the N-terminus is an amino acid other than pyroglutamic acid. As the original protein, there may be mentioned, for example, a cellulase (for example, endoglucanase, cellobiohydrolase, or β-gulucosidase), and a cellulase belonging to family 45 is preferable. In this connection, so long as the original protein has at least an endoglucanase activity, it may be a protein having only the endoglucanase activity, or a protein having one or more other enzyme activities in addition to the endoglucanase activity. Further, the original protein may be a naturally occurring protein or a genetically modified protein.

Original Source of Cellulase Belonging to Family 45

The cellulase belonging to family 45 may be generated by commonly used genetic engineering techniques, such as recombinant DNA techniques or polypeptide synthesis techniques, or may be obtained from an isolated wild-type strain. Further the cellulases include variants of wild-type cellulases belonging to family 45.

The cellulase belonging to family 45 may be obtained from a microorganism such as filamentous fungus or zygomycetes. As the filamentous fungus, there may be mentioned, for example, microorganisms belonging to genus *Humicola* (such as *Humicola insolens*), genus *Trichoderma* (such as *Trichoderma viride*), genus *Staphylotrichum* (such as *Staphylotrichum coccosporum*), or genus *Myriococcum* (such as *Myriococcum thermophilum*). More particularly, cellulases derived from genus *Humicola* include, for example, CBH I, EG V, NCE2, NCE4, and NCE5; cellulases derived from genus *Trichoderma* include, for example, CBH I, CBH II, EG II, and EG III; cellulases derived from genus *Staphylotrichum* include, for example, STCE1 and STCE3; and cellulase derived from genus *Myriococcum* include, for example, MTE1. As the zygomycetes, there may be mentioned, for example, microorganisms belonging to genus *Rhizopus* (such as *Rhizopus oryzae*), genus *Mucor* (such as *Mucor circinelloides*), or genus *Phycomyces* (such as *Phycomyces nitens*). More particularly, there may be mentioned, for example, RCE I, RCE II, or RCE III derived from *Rhizopus oryzae*; MCE I or MCE II derived from *Mucor circinelloides*; or PCE I derived from *Phycomyces nitens* (WO00/24879).

Pyroglutamic Acid or Peptide Containing Pyroglutamic Acid

The term "pyroglutamic acid" as used herein means pyroglutamic acid generated by cyclization of N-terminal glutamine or glutamic acid of a mature protein. Pyroglutamic acid has the feature that the N-terminal amino group is not exposed. Pyroglutamate formation can be performed in vivo or in vitro. In vivo, a polynucleotide encoding a modified protein, which is genetically designed so that the N-terminus of a mature protein is glutamine or glutamic acid, may be expressed in a host cell to obtain a pyroglutamate cyclation protein. In vitro, a protein having the N-terminus of glutamine or glutamic acid may be treated with an acidic solution such as formic acid to obtain a protein having the N-terminus of pyroglutamic acid.

The term "peptide" as used herein means a compound consisting of one or plural amino acids in which the amino acids are polymerized by peptide bonds. Therefore, the term "peptide containing pyroglutamic acid" as used herein means a peptide in which the N-terminal amino acid is pyroglutamic acid. The peptide containing pyroglutamic acid consists of two or more (plural) crosslinked amino acids, for example, 2 to 40 amino acids, preferably 2 to 30 amino acids, more preferably 2 to 20 amino acids, still further preferably 2 to 10, still further preferably 2 to 5, most preferably 2 to 4 amino acids. The amino acids are not particularly limited, so long as they can be used by those skilled in the art for the stated purpose.

In the method of the present invention, a method for modifying an original protein to a protein having the N-terminus of pyroglutamic acid is not particularly limited, so long as the protein modification can be performed. As the method, there may be mentioned, for example, genetic engineering techniques or chemical techniques.

According to the genetic engineering techniques, an original protein can be modified, for example, by carrying out a genetically engineered addition and/or substitution of an appropriate amino acid or amino acid sequence.

In an embodiment utilizing the genetically engineered addition, the protein modification can be carried out by genetically adding pyroglutamic acid or a peptide having the N-terminus of pyroglutamic acid, to the N-terminus of an original protein (i.e., a protein having an endoglucanase activity in which the N-terminus is not pyroglutamic acid).

More particularly, the embodiment utilizing the genetically engineered addition may comprise, for example, the steps of:

(1) adding a polynucleotide encoding an amino acid convertible into pyroglutamic acid (such as glutamic acid or glutamine) or a polynucleotide encoding a peptide having the N-terminus of an amino acid convertible into pyroglutamic acid, to the 5' terminus of a polynucleotide encoding an original protein; and (2) expressing the resulting polynucleotide in a host in which pyroglutamate formation of the N-terminal amino acid can be performed.

In an embodiment utilizing the genetically engineered substitution, the protein modification can be carried out by genetically substituting pyroglutamic acid or a peptide having the N-terminus of pyroglutamic acid, for the N-terminus amino acid or an N-terminal region of an original protein.

More particularly, the embodiment utilizing the genetically engineered substitution may comprise, for example, the steps of:

(1) substituting a polynucleotide encoding an amino acid convertible into pyroglutamic acid (such as glutamic acid or glutamine) or a polynucleotide encoding a peptide having the N-terminus of an amino acid convertible into pyroglutamic acid, for the 5' terminus or a region containing the same of a polynucleotide encoding an original protein; and (2) expressing the resulting polynucleotide in a host in which pyroglutamate formation of the N-terminal amino acid can be performed.

As embodiments utilizing the chemical techniques, there may be mentioned, for example, (a) an embodiment in which pyroglutamic acid (or a peptide having the N-terminus of pyroglutamic acid) is directly added to the N-terminus of an original protein;

(b) an embodiment in which an amino acid convertible into pyroglutamic acid (or a peptide having the N-terminus of an amino acid convertible into pyroglutamic acid) is chemically added to the N-terminus of an original protein, and then pyroglutamate formation of the N-terminal amino acid is performed chemically; or (c) an embodiment in which the N-terminal amino acid of an original protein having the N-terminus of an amino acid convertible into pyroglutamic acid is chemically converted to pyroglutamic acid.

Method for Adding Pyroglutamic Acid or peptide Containing Pyroglutamic Acid to the N-Terminal Side of Cellulase Belonging to Family 45

The modification method will be further illustrated by an embodiment using cellulase belonging to family 45. A method for adding pyroglutamic acid or a peptide containing pyroglutamic acid to the N-terminal side of cellulase belonging to family 45 may be carried out by genetic engineering techniques. In a commonly used cellulase production, a coding region of a polynucleotide encoding desired cellulase may be operably linked between a promoter and a terminator functionable in a host such as a filamentous fungus, and then the resulting expression cassette may be introduced into the host. Further, a polynucleotide encoding a signal sequence for secretion functionable in the host cell may be added to the cassette. When the cassette is introduced into the host cell, the desired cellulase is secreted into a medium, and then can be easily collected. In this case, a desired amino acid can be added to the N-terminus of cellulase, by adding a polynucleotide encoding the amino acid immediately downstream from the signal sequence for secretion. Further, the modification of the amino group in the N-terminal amino acid may be carried out by utilizing a signal sequence for secretion in a host. For example, in cbh1 or cbh2 derived from *Trichoderma viride*, or NCE2 or NCE5 derived from *Humicola insolens*, the N-terminus is formed pyroglutamate, the modification can be carried out by using these signal sequences for secretion and expressing in *Trichoderma viride* or *Humicola insolens*. According to the preferable embodiment, modified cellulase belonging to family 45 prepared as described above exhibits an advantageous feature, i.e., it has an endoglucanase activity whose reduction in the presence of a surfactant is small.

According to another embodiment, the whole can be chemically synthesized, within the scope of technical common knowledge of those skilled in the art. In this case, the synthesis may be carried out using part of a naturally-occurring protein.

Protein of the Present Invention

The protein of the present invention is prepared by modifying the N-terminus of an original protein having an endoglucanase activity to pyroglutamic acid {for example, prepared by obtaining cellulase belonging to family 45 and adding pyroglutamic acid (pQ) or a peptide containing pyroglutamic acid to the N-terminal amino acid side of the mature protein thereof}, and has an endoglucanase activity whose reduction in the presence of a surfactant is small. Further, the present invention includes a protein which may be prepared by the above-described method and has an endoglucanase activity whose reduction in the presence of a surfactant is small.

More particularly, the protein of the present invention includes a protein selected from the group consisting of the following proteins:

(a) a protein comprising the amino acid sequence of SEQ ID NO: 2, 4, 38, or 40;

(b) a modified protein comprising an amino acid sequence in which one or plural amino acids are deleted, substituted, inserted, or added in the amino acid sequence of SEQ ID NO: 2, 4, 38, or 40, and having an endoglucanase activity whose reduction in the presence of a surfactant is small; and (c) a homologous protein comprising an amino acid sequence having at least 85% homology with a protein comprising the amino acid sequence of SEQ ID NO: 2, 4, 38, or 40, and having an endoglucanase activity whose reduction in the presence of a surfactant is small.

The amino acid sequence of SEQ ID NO: 2 is the amino acid sequence of N-terminus-modified NCE4 (see Example A2) in which a peptide consisting of five amino acids (N-terminus: pyroglutamic acid) is added to the N-terminus of endoglucanase NCE4 derived from *Humicola insolens* MN200-1.

The amino acid sequence of SEQ ID NO: 4 is the amino acid sequence of N-terminus-modified STCE1 (see Example B2) in which a peptide consisting of four amino acids (N-terminus: pyroglutamic acid) is substituted for the N-terminal amino acid (Ala) of endoglucanase STCE1 derived from *Staphylotrichum coccosporum* IFO 31817.

The amino acid sequence of SEQ ID NO: 38 is the amino acid sequence of N-terminus-modified STCE1 (see Example B3) in which pyroglutamic acid is added to the N-terminus of endoglucanase STCE1 derived from *Staphylotrichum coccosporum* IFO 31817.

The amino acid sequence of SEQ ID NO: 40 is the amino acid sequence of N-terminus-modified STCE1 (see Example B4) in which a peptide consisting of four amino acids (N-terminus: pyroglutamic acid) is added to the N-terminus of endoglucanase STCE1 derived from *Staphylotrichum coccosporum* IFO 31817.

The term "modified protein" as used herein means a protein comprising an amino acid sequence in which one or plural amino acids (for example, one or several amino acids) are deleted, substituted, inserted, or added in the amino acid sequence of SEQ ID NO: 2, 4, 38, or 40, and having an endoglucanase activity whose reduction in the presence of a surfactant is small. The number of amino acids to be modified, such as "deleted, substituted, inserted, or added", is preferably 1 to 30, more preferably 1 to 10, most preferably 1 to 6.

Further, the modified protein includes a protein comprising an amino acid sequence in which one or plural amino acids are conservatively substituted in the amino acid sequence of SEQ ID NO: 2, 4, 38, or 40, and having an endoglucanase activity whose reduction in the presence of a surfactant is small. The term "conservative substitution" as used herein means that one or plural amino acid residues contained in a protein are replaced with different amino acids having similar chemical properties so that the activities of the protein are not substantially changed. As the conservative substitution, there may be mentioned, for example, a substitution of a hydrophobic amino acid residue for another hydrophobic amino acid residue, or a substitution of a polar amino acid residue for another polar amino acid residue having the same charge. Amino acids which have similar chemical properties and can be conservatively substituted with each other are known to those skilled in the art. More particularly, as nonpolar (hydrophobic) amino acids, there may be mentioned, for example, alanine, valine, isoleucine, leucine, proline, tryptophan, phenylalanine, or methionine. As polar (neutral) amino acids, there may be mentioned, for example, glycine, serine, threonine, tyrosine, glutamine, asparagine, or cysteine. As basic amino acids having a positive charge, there may be mentioned, for example, arginine, histidine, or lysine. As acidic amino acids having a negative charge, there may be mentioned, for example, aspartic acid or glutamic acid.

The term "homologous protein" as used herein means a protein comprising an amino acid sequence having at least 85% (preferably 90% or more, most preferably 95% or more) homology (sequence identity) with a protein comprising the amino acid sequence of SEQ ID NO: 2, 4, 38, or 40, and having an endoglucanase activity whose reduction in the presence of a surfactant is small. The homology as used herein is shown as the value (identity) calculated by FASTA3 {Science, 227, 1435-1441 (1985); Proc. Natl. Acad. Sci. USA, 85, 2444-2448 (1988); ddbj.nig.ac.jp/E-mail/homology-j}, a known homology search program, in accordance with default parameters.

As described above, in the "protein consisting of the amino acid sequence of SEQ ID NO: 2" of the present invention, the portion except the N-terminal peptide consisting of five amino acids is derived from endoglucanase NCE4. Further, in the "protein consisting of the amino acid sequence of SEQ ID NO: 4, 38, or 40" of the present invention, the portion except the N-terminal amino acid or peptide is derived from endoglucanase STCE1. Endoglucanases NCE4 and STCE1 belong to family 45. As known endoglucanase belonging to family 45, there may be mentioned, for example, NCE5 derived from genus *Humicola* (WO01/90375).

In FIGS. 1 and 2, an alignment of the amino acid sequences of endoglucanase STCE1 [signal peptide (SEQ ID NO: 43) and mature protein (SEQ ID NO: 44)], endoglucanase NCE4 [signal peptide (SEQ ID NO: 45) and mature protein (SEQ ID NO: 46)], and endoglucanase NCE5 [signal peptide (SEQ ID NO: 47) and mature protein (SEQ ID NO: 48)] is shown.

FIG. 1 shows the alignment of the N-terminal half, and FIG. 2 shows that of the C-terminal half. The symbol "*" in FIGS. 1 and 2 indicates an amino acid common to that in STCE1.

As shown in FIGS. 1 and 2, endoglucanases belonging to family 45 contain the catalytic domain (1st to 207th) as a common domain, and sometimes contain the Linker region (208th to 258th) and/or the cellulose-binding domain (CBD) (259th to 295th). In this connection, the numbers in parentheses after the above domains represent the amino acid numbers in the amino acid sequence (SEQ ID NO: 44) of endoglucanase STCE1.

In each region, there are many conservative amino acids between or among endoglucanases in the catalytic domain and the cellulose-binding domain, but no remarkable conservative region is observed in the Linker region. Regions containing many conservative amino acids (for example, the catalytic domain or cellulose-binding domain, particularly the catalytic domain), or common amino acids contained in the regions are considered as important regions or amino acids for the enzyme activity of endoglucanases (such as STCE1 or NCE4). Therefore, when an amino acid modification (for example, deletion, substitution, insertion, and/or addition, particularly conservative substitution) is carried out in a region or amino acid other than such important regions or amino acids, a modified or homologous protein maintaining the enzyme activity can be obtained with a high possibility, without undue experiment.

Further, even if in the regions containing many conservative amino acids, a modification of noncommon amino acid(s) between or among endoglucanases to different amino acid(S) [preferably amino acid(s) which are similar and can be conservatively substituted] may probably maintain the enzyme activity. Therefore, by such a modification, a modified or homologous protein maintaining the enzyme activity can be obtained with a high possibility, without undue experiment.

In this connection, even if common amino acid(s) in the region containing many conservative amino acids are modified to different amino acid(s), the enzyme activity is sometimes maintained. Particularly, in a modification to amino acid(s) which are similar and can be conservatively substituted, the possibility is increased. The modified or homologous protein of the present invention includes a protein in which one or more amino acids contained in any region, such as the catalytic domain, Linker region, or cellulose-binding domain, are modified, so long as it exhibits an endoglucanase activity.

Polynucleotide Encoding the Protein of the Present Invention

According to the present invention, a polynucleotide encoding a protein comprising the amino acid sequence of SEQ ID NO: 2, 4, 38, or 40, or a modified or homologous protein thereof (hereinafter collectively referred to as the protein of the present invention) may be provided. When the amino acid sequence of a protein is given, a nucleotide sequence encoding the amino acid sequence can be easily selected, and thus various nucleotide sequences encoding the protein of the present invention can be selected. The term "polynucleotide" as used herein includes DNA and RNA, and DNA is preferable.

The polynucleotide of the present invention includes a polynucleotide selected from the group consisting of the following polynucleotides:

(a) a polynucleotide comprising the nucleotide sequence of SEQ ID NO: 1, 3, 37, or 39;

(b) a polynucleotide comprising a nucleotide sequence in which one or plural nucleotides are deleted, substituted, inserted, or added in the nucleotide sequence of SEQ ID NO: 1, 3, 37, or 39, and encoding a protein having an endoglucanase activity whose reduction in the presence of a surfactant is small; and (c) a polynucleotide hybridizing under stringent conditions to a polynucleotide consisting of the nucleotide sequence of SEQ ID NO: 1, 3, 37, or 39, and encoding a protein having an endoglucanase activity whose reduction in the presence of a surfactant is small.

In the nucleotide sequence described in the above item (b), the number of nucleotides to be deleted, substituted, inserted, or added is, for example, 1 to 90, preferably 1 to 30, more preferably 1 to 18, most preferably 1 to 9.

The term "under stringent conditions" as used herein means the following conditions. In accordance with a protocol attached to an ECL direct DNA/RNA labeling and detection system (Amersham), after a polynucleotide to be tested is prehybridized at 42° C. for an hour, a polynucleotide consisting of the nucleotide sequence of SEQ ID NO: 1, 3, 37, or 39 is added, and hybridization is carried out at 42° C. for 14 to 16 hours. After the hybridization, a washing treatment with 0.5× SSC (1×SSC; 15 mmol/L sodium citrate, 150 mmol/L sodium chloride) containing 0.4% SDS and 6 mol/L urea at 42° C. for 20 minutes is repeated twice, and a washing treatment with 5×SSC at room temperature for 5 minutes is carried out twice.

The polynucleotide of the present invention includes a naturally-occurring polynucleotide. Further, the whole can be synthesized. Furthermore, the synthesis may be carried out using part of the naturally-occurring polynucleotide. Typically, the polynucleotide of the present invention may be obtained by screening a genomic library derived from a desired microorganism in accordance with an ordinary method commonly used in genetic engineering, for example, using an appropriate DNA probe designed on the basis of information of a partial amino acid sequence.

Production of the Protein of the Present Invention

The protein of the present invention can be produced in host cells by transforming the host cell with a polynucleotide molecule (particularly as a form of expression vector) comprising a polynucleotide fragment encoding the protein so that the polynucleotide molecule may be replicated and the gene may be expressed in the host cell.

According to the present invention, an expression vector comprising a polynucleotide fragment encoding the protein of the present invention so that the polynucleotide fragment may be replicated and the protein may be expressed in a host microorganism, is provided.

The expression vector of the present invention can be constructed on the basis of a self-replicating vector (such as a plasmid), which exists as an extrachromosomal element and can replicate independently of the replication of chromosomes. Alternatively, the expression vector of the present invention may be a vector which is integrated into the chromosome of the host microorganism and replicated together with chromosomes, when the host is transformed with the vector. The construction of the vector of the present invention can be carried out by ordinary procedures or methods commonly used in genetic engineering.

To express a protein having a desired activity by transforming a host microorganism with the expression vector of the present invention, it is preferable that the expression vector contains, for example, a polynucleotide capable of controlling the expression, or a genetic marker to select transformants, in addition to the polynucleotide fragment of the present invention.

As the polynucleotide capable of regulating the gene expression, various signals for the transcription or translation regulation, such as a promoter, a terminator, or a polynucleotide encoding a signal peptide for secretion, may be used in the present invention. The ligation of these polynucleotides and the insertion thereof to a vector can be carried out by an ordinary method.

The promoter which can be used in the present invention is not particularly limited, so long as it shows a transcriptional activity in a host microorganism. The promoter can be obtained as a polynucleotide which regulates the expression of a gene encoding a protein the same as or different from that derived from the host microorganism. For example, a promoter such a lactose operon or a tryptophan operon can be used in *Escherichia coli*; a promoter of an alcohol dehydrogenase gene, an acid phosphatase gene, a galactose utilization gene, or a glyceraldehyde 3-phosphate dehydrogenase gene can be used in a yeast; and a promoter of an α-amylase gene, a glucoamylase gene, a cellobiohydrolase gene, or a glyceraldehyde 3-phosphate dehydrogenase gene can be used in a filamentous fungus.

The signal peptide is not particularly limited, so long as it contributes to the protein secretion in a host microorganism. The signal peptide can be obtained as a polynucleotide derived from a gene encoding a protein same as or different from that derived from the host microorganism.

The selectable marker can be appropriately selected in accordance with the method for selecting a transformant. As the selectable marker, for example, a drug resistance gene or a gene complementing an auxotrophic mutation can be used in the present invention. When a host is a bacterium, for example, an ampicillin resistance gene, a kanamycin resistance gene, or a tetracycline resistance gene can be used. When a host is a yeast, for example, a tryptophan biosynthesis gene (trpI, trpC), an uracil biosynthesis gene (ura3), a leucine biosynthesis gene (leu2), or a histidine biosynthesis gene (his3) can be used. When a host is a filamentous fungus, for example, a destomycin resistance gene, a nitrate utilization gene (niaD), an arginine biosynthesis gene (argB), an uracil biosynthesis gene (pyr4), a hygromycin resistance gene, a bialaphos resistance gene, a bleomycin resistance gene, or an aureobasidin resistance gene can be used.

According to the present invention, a microorganism transformed with the expression vector is provided. A host-vector system which can be used in the present invention is not particularly limited. For example, a system utilizing *E. coli, Actinomycetes*, yeasts, or filamentous fungi, or a system for the expression of a fusion protein using such a microorganism can be used. When a yeast is used as a host, there may be mentioned, for example, a microorganism belonging to genus *Saccharomyces, Hansenula*, or *Pichia*, preferably *Saccharomyces cerevisiae*. When a filamentous fungus is used as a host, any filamentous fungus, preferably a microorganism belonging to genus *Humicola, Trichoderma, Aspergillus, Acremonium*, or *Fusarium*, more preferably a microorganism belonging to genus *Humicola* or *Trichoderma*, may be used. More particularly, *Humicola insolens, Humicola thermoidea, Trichoderma viride, Trichoderma reesei, Trichoderma longibrachiatum, Staphylotrichum coccosporum, Aspergillus niger, Aspergillus oryzae, Fusarium oxysporum*, or *Acremonium cellulolyticus*, preferably *Humicola insolens* or *Trichoderma viride*, may be used.

Transformation of a microorganism with the expression vector can be carried out in accordance with an ordinary method such as a calcium ion method, a lithium ion method, an electroporation method, a PEG method, an *Agrobacterium* method, or a particle gun method, and an appropriate method can be selected in accordance with a host to be transformed.

In the present invention, the transformant of the present invention is cultured, and the resulting culture is used to obtain the protein of the present invention of interest. The transformant of the present invention can be cultured in accordance with an ordinary method by appropriately selecting, for example, a medium or culture conditions.

The medium can be supplemented with, for example, carbon sources or nitrogen sources which can be anabolized or utilized, respectively, by the transformant of the present invention, inorganic salts, various vitamins, various amino acids such as glutamic acid or asparagine, trace nutrients such as nucleotides, or selective agents such as antibiotics. Further, organic and/or inorganic substances which help the growth of the transformant of the present invention or promote the production of the protein of the present invention can be appropriately added. Further, if necessary, a natural medium or synthetic medium which appropriately contains other nutrients can be used.

Any kind of carbon source and nitrogen source can be used in the medium as long as it can be utilized by the transformant of the present invention. As the anabolizable carbon source, various carbohydrates, for example, sucrose, starch, glycerin, glucose, fructose, maltose, lactose, cellulose, cellobiose, dextrin, animal oils, or plant oils, or hydrolysates thereof, can be used. Generally, the concentration thereof to the medium is preferably 0.1% to 5%. As the utilizable nitrogen source, for example, animal or plant components or extracts thereof, such as peptone, meat extract, corn steep liquor, or defatted soybean powder, organic acid ammonium salts such as succinic acid ammonium salts or tartaric acid ammonium salts, urea, or other various nitrogen-containing compounds such as inorganic or organic acids, can be used. As the inorganic salts, for example, those which can produce sodium, potassium, calcium, magnesium, cobalt, chlorine, phosphoric acid, sulfuric acid, or other ions can be appropriately used.

Any medium which contains other components, for example, cells, exudates, or extracts of microorganisms such as yeast, or fine plant powders, can be appropriately used, as long as they don't interfere with the growth of the transformant of the present invention and with the production and accumulation of the protein of the present invention. When a mutant strain having a nutritional requirement is cultured, a substance to satisfy its nutritional requirement is generally added to the medium. In this connection, such a nutrient may not necessarily be added when a medium containing natural substances is used.

The culture conditions, such as the medium component, medium fluidity, incubation temperature, agitation speed, or aeration rate, can be appropriately selected and controlled in accordance with the transformant to be used and the exterior conditions so as to obtain preferable results. If foaming occurs in a liquid medium, a defoaming agent such as silicone oils, vegetable oils, mineral oils, or surfactants can be appropriately used.

The protein of the present invention accumulated in the resulting culture is contained in the transformant of the present invention and the culture filtrate. Accordingly, it is possible to recover the protein of the present invention from both culture filtrate and transformant cells by separating the culture into each fraction by centrifugation.

The protein of the present invention can be recovered from the culture filtrate according to an ordinary method. Procedures for recovering the protein of the present invention from the culture can be carried out singly, in combination in a certain order, or repeatedly. For example, extraction filtration, centrifugation, dialysis, concentration, drying, freezing, adsorption, desorption, means for separation based on the difference in solubility in various solvents (such as precipitation, salting out, crystallization, recrystallization, reverse solution, or chromatography) can be used.

Further, the protein of the present invention can be obtained from the culture inside the transformant of the present invention. For example, extraction from the culture (for example, grinding treatment or disruption by pressure), recovery (for example, filtration or centrifugation), or purification (for example, salting out or solvent precipitation) can be carried out using an ordinary method.

The resulting crude substance can be purified according to an ordinary method, for example, by a column chromatography using a carrier such as dextran, cellulose, agarose, synthetic polymers, or silica gel. A pure protein of the present invention of interest can be obtained from the culture of the transformant of the present invention using the above-mentioned methods, either singly or in an appropriate combination.

As described above, according to another embodiment of the present invention, the process for producing the novel protein of the present invention can be provided. Cultivation of the transformant (including culturing conditions) can be carried out in a fashion substantially similar to that of the original host used to prepare the transformant. As the method for recovering the protein of interest after the cultivation of the transformant, commonly used procedures can be carried out.

Deposited Strains

*Escherichia coli* JM109 transformed with expression vector pEGD01 of the present invention (FERM BP-5973) was domestically deposited in the International Patent Organism Depositary National Institute of Advanced Industrial Science and Technology {(Former Name) National Institute of Bioscience and Human-Technology Agency of Industrial Science and Technology (Address: AIST Tsukuba Central 6, 1-1, Higashi 1-chome Tukuba-shi, Ibaraki-ken 305-8566 Japan)} on Jul. 12, 1996, and was transferred to an international deposit on Jun. 13, 1997. The international deposit number (a number in parenthesis [ ] following the international deposit number is a domestic deposit number) is FERM BP-5973 [FERM P-15729].

*Escherichia coli* JM109 transformed with expression vector pMKD01 of the present invention (FERM BP-5974) was domestically deposited in the International Patent Organism Depositary National Institute of Advanced Industrial Science and Technology {(Former Name) National Institute of Bioscience and Human-Technology Agency of Industrial Science and Technology (Address: AIST Tsukuba Central 6, 1-1, Higashi 1-chome Tukuba-shi, Ibaraki-ken 305-8566 Japan)} on Jul. 12, 1996, and was transferred to an international deposit on Jun. 13, 1997. The international deposit number (a number in parenthesis [ ] following the international deposit number is a domestic deposit number) is FERM BP-5974 [FERM P-15730].

*Escherichia coli* JM109 transformed with expression vector pCB1-M2XR of the present invention (FERM BP-6045) was domestically deposited in the International Patent Organism Depositary National Institute of Advanced Industrial Science and Technology {(Former Name) National Institute of Bioscience and Human-Technology Agency of Industrial Science and Technology (Address: AIST Tsukuba Central 6, 1-1, Higashi 1-chome Tukuba-shi, Ibaraki-ken 305-8566 Japan)} on Sep. 9, 1996, and was transferred to an international deposit on Aug. 11, 1997. The international deposit number (a number in parenthesis [ ] following the international deposit number is a domestic deposit number) is FERM BP-6045 [FERM P-15840].

In this connection, plasmid pCB1-M2 of the present invention can be obtained, not only by the method described in EXAMPLES, but also by self-ligation of the plasmid pCB1-M2XR previously digested with restriction enzyme XbaI.

*Humicola insolens* MN200-1 (FERM BP-5977), which may be used as a host for the expression vector of the present invention, was domestically deposited in the International Patent Organism Depositary National Institute of Advanced Industrial Science and Technology {(Former Name) National Institute of Bioscience and Human-Technology Agency of Industrial Science and Technology (Address: AIST Tsukuba Central 6, 1-1, Higashi 1-chome Tukuba-shi, Ibaraki-ken 305-8566 Japan)} on Jul. 15, 1996, and was transferred to an international deposit on Jun. 13, 1997. The international deposit number (a number in parenthesis [ ] following the international deposit number is a domestic deposit number) is FERM BP-5977 [FERM P-15736].

*Trichoderma viride* MC300-1 (FERM BP-6047), which may be used as a host for the expression vector of the present invention, was domestically deposited in the International Patent Organism Depositary National Institute of Advanced Industrial Science and Technology {(Former Name) National Institute of Bioscience and Human-Technology Agency of Industrial Science and Technology (Address: AIST Tsukuba Central 6, 1-1, Higashi 1-chome Tukuba-shi, Ibaraki-ken 305-8566 Japan)} on Sep. 9, 1996, and was transferred to an international deposit on Aug. 11, 1997. The international deposit number (a number in parenthesis [ ] following the international deposit number is a domestic deposit number) is FERM BP-6047 [FERM P-15842].

*Escherichia coli* DH5α transformed with expression vector pUC118-STCEex of the present invention (FERM BP-10127) was domestically deposited in the International Patent Organism Depositary National Institute of Advanced Industrial Science and Technology (Address: AIST Tsukuba Central 6, 1-1, Higashi 1-chome Tukuba-shi, Ibaraki-ken 305-8566 Japan) on Dec. 1, 2003, and was transferred to an international deposit on Sep. 15, 2004. The international deposit number (a number in parenthesis [ ] following the international deposit number is a domestic deposit number) is FERM BP-10127 [FERM P-19602]. In this connection, plasmid pUC118-STCEex is a plasmid obtained by inserting the STCE gene into the BamHI site of plasmid pUC118. The endoglucanase STCE1 gene present in the BamHI fragment contains an intron and has the sequence of SEQ ID NO: 5.

EXAMPLES

The present invention now will be further illustrated by, but is by no means limited to, the following Examples.

Example A1

Construction of Expression Vectors for Expressing N-Terminus-Modified Cellulase and Wild-Type Cellulase in *Humicola insolens*

(1) Construction of Expression Vector pMKD01 for Expressing N-Terminus-Modified Cellulase Plasmid pUC118 (Takara Bio) was digested with BamHI. The resulting fragment was blunted with a DNA blunting kit (Takara Bio), and self-ligated with a DNA ligation kit (Takara Bio) to obtain pUC118-BN. The pUC118-BN was digested with SphI, blunted, and self-ligated to obtain pUC118BSN. Next, a 3.4-kb PstI-XbaI fragment comprising the cellulase NCE2 gene was obtained from *Humicola insolens* MN200-1 (FERM BP-5977) in accordance with the method described in Japanese Unexamined Patent Publication (Kokai) No. 8-126492. The fragment was ligated with pUC118BSN previously digested with the same restriction enzyme to obtain pUC118BSN-PX. Site-directed mutation was introduced into pUC118BSN-PX with a Sculptor in vitro mutagenesis system (Amersham Bioscience) to obtain plasmid pM21. As oligonucleotides for mutagenesis, oligonucleotides MNC-02 and MNC-03 were used.

(SEQ NO: 6)
MNC-02: 5'-GAGCGCCAGAACTGTGGATCCACTTGGTGAGCAATG-3'

(SEQ NO: 7)
MNC-03: 5'-TCCGCCGTTCTGAGCGGATCCAGGCGTTTGGCGCG-3'

The plasmid pM21 was digested with BamHI, and ligated with a BamHI-digested PCR fragment of a cellobiohydrolase gene (NCE3) derived from *Humicola insolens* MN200-1 to obtain plasmid pKM04. The PCR fragment of the NCE3 was amplified using genomic DNA (WO98/03640) from *Humicola insolens* MN200-1 (FERM BP-5977) as a template and the following primers MKA-05 and MKA-06.

(SEQ NO: 8)
MKA-05: 5'-GCCGCCCAGCAGGCGGGATCCCTCACCACCGAGAGG-3'

(SEQ NO: 9)
MKA-06: 5'-TGATCGTCGAGTCAGGGATCCAGAATTTACAGGCAC-3'

Next, a promoter and a terminator (Mullaney, E. J. et. al., Mol. Gen. Genet., 199, 37-45, 1985) of the trpC gene derived from *Aspergillus nidulans* were used to prepare a gene capable of expressing a destomycin resistance gene in *Humicola insolens*. The resulting gene was ligated with plasmid pKM04 previously digested with XbaI to construct expression vector pMKD01 (FERM BP-5974) for expressing N-terminus-modified cellulase. In pMKD01, the BamHI recognition sites were introduced at the 10 bp downstream from the N-terminus of the mature protein of the NCE2 gene and at the 3 bp downstream from the stop codon thereof, and thus five amino acid residues can be added to the N-terminus of a desired cellulase belonging to family 45.

TABLE 1

|  |
| --- |
| BamHI                    BamHI |
| 5'-GAGCGCCAGAACTGT<u>GGATCC</u>CTC---TGCCTGTAAGc<u>ggatcc</u>agg-3'   (SEQ NO: 10) |
|      GluArg<u>Gln</u>AsnCysGlySerLeu---CysLeu                (SEQ NO: 11) |
|         ↑N-terminus of mature protein |

(2) Construction of Expression Vector pJD01 for Expressing Wild-Type Cellulase

Site-directed mutation was introduced, using oligonucleotide pMN-Bam, into plasmid pM21 obtained in the above item (1) to obtain plasmid pM21-m-A1.

pMN-Bam:
(SEQ NO: 12)
5'-GGTCAAACAAGTCTGTGCGGATCCTGGGACAAGATGGCCAAGTTCTTCCTTAC-3'

Plasmid pM21-m-A1 was digested with restriction enzymes HindIII and BamHI, and the resulting fragment of approximately 1 kb was recovered. Next, pMKD01 obtained in Example A1(1) was digested with HindIII and BamHI, and a fragment of approximately 7 kb was recovered. These fragments were ligated to obtain plasmid pJD01. In this vector, the BamHI recognition sites were introduced at the 15 bp upstream from the translation initiation site of the NCE2 gene and at the 3 bp downstream from the stop codon thereof, and thus a desired cellulase belonging to family 45 was expressed from the transcription initiation point.

TABLE 2

|  |
| --- |
| BamHI                        BamHI |
| 5'-tgc<u>ggatcc</u>tgggacaagATGGCC---CCGTTCTGAGc<u>ggatcc</u>agg-3'   (SEQ NO: 13) |
|                   MetAla---ProPhe                      (SEQ NO: 14) |

Example A2

Construction of Expression Vectors for Expressing Wild-Type NCE4 and N-Terminus-Modified NCE4, Transformation of *Humicola insolens* Therewith, and Evaluation of Activities (1) Construction of Expression Vectors As an expression vector for wild-type NCE4, the coding region of the NCE4 gene was ligated with pJD01 obtained in Example A1(2) to construct pN2EX-N4.

First, the coding region of the NCE4 gene was amplified by carrying out PCR using genomic DNA from *Humicola insolens* MN200-1 as a template and NCE4-Ne and NCE4-Ce as primers. The resulting PCR product of approximately 0.9 kbp was digested with BamHI, and ligated with pJD01 previously digested with the same restriction enzyme to construct pN2EX-N4.

```
                                              (SEQ NO: 15)
NCE4-Ne: 5'-GGGGGGATCCTGGGACAAGATCCGTTCCTCCCCTCTC-3'

(SEQ NO: 16)
NCE4-Ce: 5'-GGGGGGATCCCTGCGTTTACAGGCACTGATGG-3'
```

As an expression vector for N-terminus-modified NCE4, the coding region of the mature protein in which the signal sequence for secretion was deleted in the NCE4 gene was ligated with pMKD01 (FERM BP-5974) obtained in Example A1 (1) to construct pEGD01 (FERM BP-5973). First, the coding region of the mature protein part of the NCE4 gene was amplified by carrying out PCR using genomic DNA from *Humicola insolens* MN200-1 as a template and NCE4-Ns and NCE4-Cs as primers. The resulting PCR product of approximately 0.8 kbp was digested with BamHI, and ligated with pMKD01 previously digested with the same restriction enzyme to construct pEGD01.

```
                                              (SEQ NO: 17)
NCE4-Ns: 5'-CCGGTGTTGGCCGGATCCGCTGATGGCAAG-3'

(SEQ NO: 18)
NCE4-Cs: 5'-TAAGGCCCTCAAGGATCCCTGCGTCTACAG-3'
```

(2) Transformant Containing Wild-Type NCE4 or N-Terminus-Modified NCE4

*Humicola insolens* MN200-1 was cultured in an S medium (3.0% glucose, 2.0% yeast extract, 0.1% polypeptone, 0.03% calcium chloride, and 0.03% magnesium sulfate; pH6.8) at 37° C. for 24 hours. The resulting mycelia were collected by centrifugation, washed with 0.5 mol/L sucrose, and suspended in 0.5 mol/L sucrose solution containing 3 mg/mL β-glucuronidase (Sigma), 1 mg/mL chitinase, and 1 mg/mL zymolyase 20T (Seikagaku Corp.). The suspension was gently shaken at 30° C. for 60 to 90 minutes to generate protoplasts. The resulting protoplasts were collected by filtration and centrifugation, washed with an SUTC buffer (0.5 mol/L sucrose, 10 mmol/L calcium chloride, and 10 mmol/L Tris-HCl; pH7.5), and resuspended in SUTC to prepare a protoplast suspension.

To 100 μL of the protoplast suspension, 10 μL of each DNA solution (pEGD01 or pN2EX-N4) was added. After each was allowed to stand on ice for 5 minutes, 400 μL of a PEG solution (60% polyethylene glycol 4000, 10 mmol/L calcium chloride, and 10 mmol/L Tris-HCl; pH7.5) was added, and the whole was allowed to stand on ice for 20 minutes. After the resulting protoplast suspension was washed with the SUTC buffer, a YMG medium (1% glucose, 0.4% yeast extract, 0.2% malt extract, and 1% agar; pH6.8) containing 200 μg/mL hygromycin B was overlaid with the protoplast suspension together with YMG soft agar. The plate was incubated at 37° C. for 5 days to obtain transformants as colonies.

(3) Comparison of Endoglucanase Activities of Wild-Type NCE4 and N-Terminus-Modified NCE4 in Culture Supernatants The resulting transformants were cultured in accordance with the method described in WO98/03667, to obtain culture supernatants. The culture supernatants were subjected to SDS-PAGE, to select culture supernatants in which the NCE4 band of approximately 43 kDa was clearly detected. The endoglucanase activities in the culture supernatants at pH10 in the absence and presence of LAS were measured, and the degrees of a reduction in the activity in the presence of LAS were compared. The results are shown in Table 3. In Table 3, the endoglucanase activities are represented by percentages when each endoglucanase activity at pH10 is regarded as 100.

TABLE 3

|  | Expression vector | EGU (%) Without LAS | EGU (%) With LAS |
|---|---|---|---|
| Wild-type NCE4 | pN2EX-N4 | 100 | 27.1 |
| N-terminus-modified NCE4 | pEGD01 | 100 | 55.6 |

As a result, the culture supernatant obtained from the N-terminus-modified NCE4 transformant exhibited a small reduction in the activity in the presence of LAS. Upon a comparison of the endoglucanase activities in the presence of LAS, it was found that the endoglucanase activity of N-terminus-modified NCE4 was 2.1 times higher than that of wild-type NCE4. Further, the endoglucanase activity of *Humicola insolens* MN200-1 accounted for approximately 4% of the transformant, and thus it was found that almost all of the endoglucanase activities were derived from the recombinant enzymes expressed by the incorporated expression vectors.

(4) Analysis of N-Terminal Amino Acid Sequences of Wild-Type NCE4 and N-Terminus-Modified NCE4

Culture supernatants of the above transformants were subjected to SDS-PAGE, and the electrophoresed proteins were electrically transferred on a PVDF membrane (Immobilon-PSQ; Millipore). The NCE4 bands of approximately 43 kDa were excised from the blot, and subjected to Protein Sequencer Model 492 (Applied Biosystems) to analyze the amino acid sequences.

As a result, it was confirmed that the sequence of wild-type NCE4 obtained from the pN2EX-N4 transformant was consistent with the DNA sequence of NCE4 derived from *Humicola insolens* MN200-1 described in WO98/03667.

However, the amino acid sequence of N-terminus-modified NCE4 obtained from the pEGD01 transformant could not be determined in the above procedure. A Pfu pyroglutamate aminopeptidase (Takara Bio) was used to remove the modified N-terminus from N-terminus-modified NCE4, and then the amino acid was determined (SEQ NO: 2).

The results were summarized in Table 4, to compare the N-terminal amino acids and the N-terminal amino acid sequences in wild-type NCE4 and N-terminus-added NCE4, and it was confirmed from the results that each NCE4 had the N-terminal amino acid sequence expected from the corresponding constructed expression vector.

TABLE 4

| | N-terminal amino acid | N-terminal amino acid sequence |
|---|---|---|
| Wild-type NCE4 | Alanine (unmodified) | ADGKSTR (SEQ NO: 19) |
| N-terminus-modified NCE4 | Pyroglutamic acid (modified) | pQNCGSADGKSTR (SEQ NO: 20) |

Example B1

Construction of Expression Vectors for *Trichoderma viride* for Expressing N-Terminus-Modified Cellulase and Wild-Type Cellulase (1) Construction of Expression Vectors From a PstI fragment of 7 kb containing the cbh1 gene derived from *Trichoderma viride* MC300-1 (obtained in accordance with WO98/11239), a HindIII fragment of approximately 3.1 kb containing a cbh1 promoter region, and a SalI fragment of 2.7 kb containing a cbh1 terminator region were cloned into plasmid pUC119 to construct plasmid pCB1-H4 and plasmid pCB1-S1, respectively. *E. coli* JM109 containing each resulting plasmid was infected with helper phage M13K07 to obtain each single-stranded DNA. To the resulting single-stranded DNAs of plasmids pCB1-H4 and pCB1-S1 as templates, phosphorylated oligonucleotides CBn-Stu and CBc-Xho were annealed, and mutations were introduced by a Sculptor in vitro mutagenesis system (Amersham Bioscience), to construct plasmids pCB1H4-19 and pCB1S1-17, respectively. An approximately 6 kb fragment, which had been obtained by digesting plasmid pCB1H4-19 with XbaI and XhoI, was ligated with an approximately 1.2 kb fragment, which had been obtained by digesting plasmid pCB1S1-17 with XbaI and then partially digesting it with XhoI, to construct pCB1-M.

```
                                                  (SEQ NO: 21)
CBn-Stu: 5'-GATACATGATGCGCAGGCCTTAGTCGACTAGAATGC-
3'

(SEQ NO: 22)
CBc-Xho: 5'-GATCCTCAAGCTTTTGCTCGAGTACCTTACAAGCAC-
3'
```

Next, an approximately 2.7 kb fragment obtained by digesting pCB1-M with SalI was cloned into plasmid pUC119 to construct plasmid pCB1-SalM. To a single-strand DNA obtained from plasmid pCB1-SalM, phosphorylated oligonucleotides CB1-SmSph, CB1-Bam, and CB1-Pst were annealed, and mutations were introduced by the Sculptor in vitro mutagenesis system.

```
                                                  (SEQ NO: 23)
CB1-SmSph: 5'-GGAGGGTGCATGCCGACTGAGCCCGGGCAGTAGCC-
3'

(SEQ NO: 24)
CB1-Bam:  5'-GCCGGGAGAGGATCCAGTGGAGG-3'

(SEQ NO: 25)
CB1-Pst:  5'-GCTCGAGTACCTTACTGCAGGCACTGAGAG-3'
```

Next, plasmid pUC118 was digested with XbaI and EcoRI, blunted with the DNA blunting kit, and self-ligated, to construct plasmid pUC118-SBN. To pUC118-SBN digested with HindIII and SalI, the cbh1 promoter fragment of approximately 1.4 kb previously digested with the same restriction enzymes was inserted. The resulting plasmid was digested with SalI, and ligated with the mutations-introduced cbh1 coding region and terminator region of approximately 2.8 kb, to construct pCB1-M2. The introduced mutations (excluding the BamHI mutation) are shown in Table 5.

TABLE 5

```
     SalI    StuI
5'-ctagtcgactaaggcctgcgcatcATGTATGAAAAGTTGGCCCTCATCTCGGCCTTCTTGGCTACT   (SEQ NO: 26)
                            MetTyrGlnLysLeuAlaLeuIleSerAlaPheLeuAlaThr    (SEQ NO: 27)

SmaI        SphI                  PstI         XhoI    HindIII        (SEQ NO: 28)
5'-GCCCGGGCTCAGTCGGCATGCACC---CAGTGCCTGCAGTAAggtactcgagcaaaagcttgag-3'   (SEQ NO: 29)
   AlaArgAlaGlnSerAlaCysThr---GlnCysLeuGln
                ↑N-terminus of mature protein
```

Example B2

Construction of Expression Vectors for Expressing N-Terminus-Modified STCE1 and Wild-Type STCE1, Transformation of *Trichoderma viride* Therewith, and Evaluation of Activities (1) Construction of Expression Vectors As an expression vector for wild-type STCE1, the coding region of the STCE1 gene was ligated with plasmid pCB1-M2 obtained in Example B1 to construct pCB-Ste.

First, the coding region of the STCE1 gene was amplified by carrying out PCR using plasmid pUC118-STCEex (FERM BP-10127) as a template and the combination of primers STCE1-TNERV and STCE1-TCET22I. The resulting PCR product of approximately 1 kbp was digested with EcoRV and EcoT22I, and ligated with pCB1-M2 previously digested with StuI and PstI to construct pCB-Ste.

```
                                                  (SEQ NO: 30)
STCE1-TNERV: GGGGATATCGCGCATCATGCGTTCCTCCCCCGTCCTC (SEQ NO: 31)
STCE1-TCET22I: GGGATGCATTTAAAGGCACTGCGAGTACCAGTC
```

As an expression vector for N-terminus-modified STCE1, the coding region of the mature protein in which the signal sequence for secretion was deleted in the STCE1 gene was ligated with pCB1-M2 obtained in Example B1 to construct pCB-Sts.

First, the coding region of the mature protein of the STCE1 gene was amplified by carrying out PCR using plasmid pUC118-STCEex (FERM BP-10127) as a template and STCE1-TmNSph and STCE1-TCET22I as primers. The resulting PCR product of approximately 1 kbp was digested with SphI and EcoT22I, and ligated with pCB1-M2 previously digested with SphI and PstI to construct pCB-Sts.

STCE1-TmNSph: GGGGCATGCGATGGCAAGTCGACCCGCTAC (SEQ NO: 32)

(2) Generation of *Trichoderma viride* Strain 2

A suspension (approximately $10^9$ CFU/mL) of spores of *Trichoderma viride* MC300-1 (FERM BP-6047) was irradiated with UV from two UV lamps located at a height of 30 cm thereabove while gently shaking. The suspension was spread on a selection medium, and cultured at 28° C. for 7 days. The grown strains were selected to obtain *Trichoderma viride* strain 2 showing uracil requirement.

In this connection, the selection medium was a minimal medium [0.2% potassium dihydrogenphosphate, 0.4% ammonium sulfate, 0.03% urea, 0.03% magnesium sulfate heptahydrate, 0.03% calcium chloride, 0.5% glucose, 2.5% agar, and 0.01% trace elements (prepared by dissolving 5 mg iron sulfate heptahydrate, 1.56 mg manganese sulfate heptahydrate, 1.4 mg zinc sulfate heptahydrate, and 2 mg cobalt chloride in 1 L of water)] supplemented with 10 µg/mL uridine and 1 mg/mL 5-fluoroorotic acid.

(3) Transformant Containing Wild-Type STCE1 or N-Terminus-Modified STCE1

*Trichoderma viride* was transformed with pCB-Ste or pCB-Sts obtained in Example B2(1), by carrying out a co-transformation method using Trichoderma viride strain 2 obtained in Example B2(2) and marker plasmid pPYR4 containing the pyr4 gene derived from *Neurospora crassa*, to obtain transformants as strains grown in the minimal medium.

First, *Trichoderma viride* strain 2 was inoculated in a 200 mL conical flask containing 50 mL of a mycelium formation medium {1% yeast extract, 1% malt extract, 2% polypeptone, 2.5% glucose, 0.1% dipotassium hydrogenphosphate, 0.05% magnesium sulfate heptahydrate, and 0.0001% uridine (pH7.0)}, and cultured at 28° C. for 2 days. The resulting cells were collected by centrifugation, washed with 0.5 mol/L sucrose, and suspended in 0.5 mol/L sucrose solution containing 3 mg/mL β-glucuronidase (Sigma), 1 mg/mL chitinase, and 1 mg/mL zymolyase 20T (Seikagaku Corp.). The suspension was gently shaken at 30° C. for 60 to 90 minutes to generate protoplasts. The resulting protoplasts were collected by filtration and centrifugation, washed with the SUTC buffer, and resuspended in SUTC to prepare a protoplast suspension.

To 100 µL of the protoplast suspension, 10 µL of each DNA solution (pCB-Ste or pCB-Sts) was added. After each was allowed to stand on ice for 5 minutes, 400 µL of the PEG solution was added, and the whole was allowed to stand on ice for 20 minutes. After the resulting protoplast suspension was washed with the SUTC buffer, the minimal medium containing 0.5 mol/L sucrose was overlaid with the protoplast suspension together with soft agar. The plate was incubated at 28° C. for 5 days, and then grown colonies were transferred on the minimal medium, to obtain transformants as colonies grown thereon.

(4) Comparison of Endoglucanase Activities of Wild-Type STCE1 and N-Terminus-Modified STCE1 in Culture Supernatants The resulting transformants were cultured in accordance with the method described in WO98/11239, to obtain culture supernatants. The culture supernatants were subjected to SDS-PAGE, to select culture supernatants in which the STCE1 band of approximately 45 kDa was clearly detected. The endoglucanase activities in the culture supernatants at pH10 in the absence and presence of LAS were measured, and the degrees of a reduction in the activity in the presence of LAS were compared. The results are shown in Table 6. In Table 6, the endoglucanase activities are represented by percentages when each endoglucanase activity at pH10 is regarded as 100.

TABLE 6

| | Expression vector | EGU (%) | |
|---|---|---|---|
| | | Without LAS | With LAS |
| Wild-type STCE1 | pCB-Ste | 100 | 14.5 |
| N-terminus-modified STCE1 | pCB-Sts | 100 | 25.9 |

As a result, on comparison of the endoglucanase activities in the presence of LAS, it was found that the endoglucanase activity of N-terminus-modified STCE1 was approximately 1.8 times higher than that of wild-type STCE1. Further, the endoglucanase activity of *Trichoderma viride* strain 2 was not detected, and thus it was found that the endoglucanase activities were derived from the recombinant enzymes expressed by the incorporated expression vectors.

(5) Analysis of N-Terminal Amino Acid Sequences of Wild-Type STCE1 and N-Terminus-Modified STCE1

From each culture supernatant of the above transformants, a solution thereof containing 0.05 mol/L Tris-HCl (pH8.0)/1 mol/L sodium sulfate was prepared, and adsorbed to an equal bed volume (BV) of TOYOPEARL Butyl-650S (Tosoh Corporation). The carriers were washed with three BVs of 0.05 mol/L Tris-HCl (pH8.0)/1 mol/L sodium sulfate to remove non-adsorption components. The elution was carried out with three BVs of 0.05 mol/L Tris-HCl (pH8.0)/0.5 mol/L sodium sulfate, and, the eluted solution was concentrated by Pellicon XL (cut 5000; Millipore) and Ultrafree-15 (cut 5000; Millipore). From the obtaining concentrate, a solution thereof containing 0.1 mol/L sodium phosphate (pH5.8)/1 mol/L ammonium sulfate was prepared. The resulting solution was subjected to a hydrophobic chromatography using Resource PHE (6 mL; Amersham Bioscience), to recover a non-adsorption fraction. The non-adsorption fraction was concentrated, and desalted by PD-10 (Amersham Bioscience), and, from the fraction, a solution thereof containing 0.05 mol/L Tris-HCl (pH7.5) solution was prepared. The solution was subjected to Resource Q (6 mL; Amersham Bioscience), to recover a non-adsorption fraction. The non-adsorption fraction was desalted and, from the fraction, a solution thereof containing 0.05 mol/L sodium acetate (pH5.0) solution was prepared. The solution was subjected to Resource S (6 mL; Amersham Bioscience), to recover a non-adsorption fraction. The non-adsorption fraction was concentrated and subjected to a gel chromatography using Superdex 75 pg (16×60 mm; Amersham Bioscience) to recover a fraction having a fractionated molecular weight of approximately 45000. Each fraction (derived from each culture supernatant of the above transformants) contained only the single band of 45 kDa.

The purified fractions were subjected to SDS-PAGE, and the electrophoresed proteins were electrically transferred on a PVDF membrane. The STCE1 bands of approximately 45 kDa were excised from the blot, and subjected to Protein Sequencer Model 492 (Applied Biosystems) to analyze the amino acid sequences.

As a result, it was confirmed that the sequence of wild-type STCE1 obtained from the pCB-Ste transformant was consistent with the DNA sequence (SEQ ID NO: 5) of STCE1 derived from *Staphylotrichum coccosporum* IFO (present name: NBRC) 31817.

However, the amino acid sequence of STCE1 obtained from the N-terminus-modified STCE1 transformant could not be determined in the above procedure. A Pfu pyroglutamate aminopeptidase (Takara Bio) was used to remove the modified N-terminus from N-terminus-modified STCE1, and then the amino acid was determined (SEQ NO: 4).

The results were summarized in Table 7 to compare the N-terminal amino acids and the N-terminal amino acid sequences in wild-type STCE1 and N-terminus-modified STCE1. It was confirmed from the results that each STCE1 had the N-terminal amino acid sequence expected from the corresponding constructed expression vector.

TABLE 7

|  | N-terminal amino acid | N-terminal amino acid sequence |
|---|---|---|
| Wild-type STCE1 | Alanine (unmodified) | ADGKSTR (SEQ NO: 33) |
| N-terminus-modified STCE1 | Pyroglutamic acid (modified) | pQSACDGKSTR (SEQ NO: 34) |

(6) Comparison of Endoglucanase Activities of Purified Wild-Type STCE1 and Purified N-Terminus-Modified STCE1

The endoglucanase activities of purified wild-type STCE1 and purified N-terminus-substituted STCE1 obtained in Example B2(5) at pH10 in the absence and presence of LAS were measured, and the degrees of a reduction in the activity in the presence of LAS were compared. The results are shown in Table 8. In Table 8, the endoglucanase activities are represented by percentages when each endoglucanase activity at pH10 is regarded as 100.

TABLE 8

|  | EGU (%) | |
|---|---|---|
|  | Without LAS | With LAS |
| Purified wild-type STCE1 | 100 | 16.2 |
| Purified N-terminus-modified STCE1 | 100 | 30.0 |

As a result, on comparison of the endoglucanase activities in the presence of LAS, it was found that the endoglucanase activity of purified N-terminus-modified STCE1 was approximately 1.9 times higher than that of purified wild-type STCE1.

Example B3

Change of N-Terminal Sequence Added to STCE1, Construction of Vector, Transformation of *Trichoderma viride* Therewith, and Evaluation of Activities (1) Construction of Expression Vector for Adding Only Pyroglutamic Acid to the N-Terminus of mature Protein As an expression vector for STCE1 in which only pyroglutamic acid was added, the coding region of the mature protein in which the signal sequence for secretion was deleted in the STCE1 gene was ligated with plasmid pCB1-M2 obtained in Example B1 to construct pCB-Stm11.

First, the coding region of the mature protein of the STCE1 gene was amplified by carrying out PCR using plasmid pUC118-STCEex (FERM BP-10127) as a template and STCE-TmNSma and STCE1-TCET22I as primers. The resulting PCR product of approximately 1 kbp was digested with SmaI and EcoT22I, and ligated with pCB1-M2 previously digested with SmaI and PstI to construct pCB-Stm11. *Trichoderma viride* transformed with vector pCB-Stm11 constructed as above produces STCE1 having the N-terminal amino acid sequence of PQADGKSTR (SEQ ID NO: 41) {i.e., the sequence in which one pyroglutamic acid (pQ) is added to the N-terminus of wild-type STCE1}.

(SEQ NO: 35)
STCE-TmNSma: GGCCCGGGCTCAGGCCGATGGCAAGTCGACCCG (2) Comparison of Endoglucanase Activity of Pyroglutamic Acid-Added STCE1

*Trichoderma viride* strain 2 was transformed with pCB-Stm11 in accordance with the procedure described in Example B2(3). The resulting transformants were cultured in accordance with WO98/11239 to obtain culture supernatants. The culture supernatants were subjected to SDS-PAGE, to select a culture supernatant in which the STCE1 band of approximately 45 kDa was clearly detected. The endoglucanase activity in the culture supernatant at pH10 in the absence and presence of LAS were measured, and the degree of a reduction in the activity in the presence of LAS was compared to that of wild-type STCE1 in Example B2(4). The results are shown in Table 9. In Table 9, the endoglucanase activities are represented by percentages when each endoglucanase activity at pH10 is regarded as 100.

TABLE 9

|  | Expression vector | EGU (%) | |
|---|---|---|---|
|  |  | Without LAS | With LAS |
| Wild-type STCE1 | pCB-Ste | 100 | 14.5 |
| pQ-added STCE1 | pCB-Stm11 | 100 | 23.0 |

As a result, on comparison of the endoglucanase activities in the presence of LAS, it was found that the endoglucanase activity of pyroglutamic acid-added STCE1 was approximately 1.6 times higher than that of wild-type STCE1.

Example B4

Change of N-Terminal Sequence Added to STCE1, Construction of Vector, Transformation of *Trichoderma viride* Therewith, and Evaluation of Activities (1) Construction of Expression Vector for Adding pQ-Containing 4 Amino Acids to the N-Terminus of Mature Protein As an expression vector for STCE1 in which 4 amino acids containing pyroglutamic acid were added, the coding region of the mature protein in which the signal sequence for secretion was deleted in the STCE1 gene was ligated with plasmid pCB1-M2 obtained in Example B1 to construct pCB-Stm12.

First, the coding region of the mature protein of the STCE1 gene was amplified by carrying out PCR using plasmid pUC118-STCEex (FERM BP-10127) as a template and STCE-TmNSph-2 and STCE1-TCET22I as primers. The resulting PCR product of approximately 1 kbp was digested with SphI and EcoT22I, and ligated with pCB1-M2 previously digested with SphI and PstI to construct pCB-Stm12. *Trichoderma viride* transformed with vector pCB-Stm12 constructed as above produces STCE1 having the N-terminal amino acid sequence of pQSACADGKSTR (SEQ ID NO: 42) {i.e., the sequence in which a peptide consisting of 4 amino acids (the N-terminus is pyroglutamic acid) is added to the N-terminus of wild-type STCE1}.

```
                                              (SEQ NO: 36)
STCE-TmNSph-2: GGGCATGCGCCGATGGCAAGTCGACCCGC
```

(2) Comparison of Endoglucanase Activity of pQ-Containing 4-Amino-Acids-Added STCE1

*Trichoderma viride* strain 2 was transformed with pCB-Stm12 in accordance with the procedure described in Example B2(3). The resulting transformants were cultured in accordance with WO98/11239 to obtain culture supernatants. The culture supernatants were subjected to SDS-PAGE, to select a culture supernatant in which the STCE1 band of approximately 45 kDa was clearly detected. The endoglucanase activity in the culture supernatant at pH10 in the absence and presence of LAS were measured, and the degree of a reduction in the activity in the presence of LAS was compared to that of wild-type STCE1 in Example B2(4). The results are shown in Table 10. In Table 10, the endoglucanase activities are represented by percentages when each endoglucanase activity at ph10 is regarded as 100.

TABLE 10

| | Expression vector | EGU (%) | |
| --- | --- | --- | --- |
| | | Without LAS | With LAS |
| Wild-type STCE1 | pCB-Ste | 100 | 14.5 |
| pQ-containing 4-AAs-added STCE1 | pCB-Stm12 | 100 | 22.4 |

As a result, on comparison of the endoglucanase activities in the presence of LAS, it was found that the endoglucanase activity of pQ-containing 4-amino-acids-added STCE1 (pQ-containing 4-AAs-added STCE1) was approximately 1.5 times higher than that of wild-type STCE1.

INDUSTRIAL APPLICABILITY

The protein of the present invention exhibits a small reduction in an endoglucanase activity in the presence of a surfactant, in comparison with wild-type cellulases, and thus is useful as a component of a detergent for clothing.

Although the present invention has been described with reference to specific embodiments, various changes and modifications obvious to those skilled in the art are possible without departing from the scope of the appended claims.

BRIEF DESCRIPTION OF THE DRAWINGS

FIG. 1 shows the results of comparison among the amino acid sequence of endoglucanase STCE1 [signal peptide (SEQ ID NO: 43) and mature protein (SEQ ID NO: 44)] and the amino acid sequences of known endoglucanases belonging to family 45, NCE4 [signal peptide (SEQ ID NO: 45) and mature protein (SEQ ID NO: 46)] and NCE5 [signal peptide (SEQ ID NO: 47) and mature protein (SEQ ID NO: 48)], with respect to the amino acid sequences of N-terminal half.

FIG. 2 shows the results of the comparison described in FIG. 1, with respect to the amino acid sequences of C-terminal half.

FREE TEXT IN SEQUENCE LISTING

Features of "Artificial Sequence" are described in the numeric identifier <223> in the Sequence Listing. Each of the nucleotide sequences of SEQ ID NOS: 6-10, 12-13, 15-18, 21-26, 28, 30-32, and 35-36 is primer MNC-02, primer MNC-03, primer MKA-05, primer MKA-06, pMKD01, primer pMN-Bam, pJD01, primer NCE4-Ne, primer NCE4-Ce, primer NCE4-Ns, primer NCE4-Cs, primer CBn-Stu, primer CBc-Xho, primer CB1-SmSph, primer CB1-Bam, primer CB1-Pst, pCB1-M2, pCB1-M2, primer STCE1-TNERV, primer STCE1-TCET22I, primer STCE1-TmNSph, primer STCE1-TmNSma, and primer STCE1-TmNSph-2. Each of the amino acid sequences of SEQ ID NOS: 11, 14, 27, and 29 is pMKD01, pJD01, pCB1-M2, and pCB1-M2.

The invention claimed is:

1. An isolated protein selected from the group consisting of:
   (a) a protein comprising the amino acid sequence of SEQ ID NO: 2, 4, 38, or 40, wherein the N-terminal amino acid is pyroglutamic acid; and
   (b) a protein comprising an amino acid sequence having at least 95% identity to the amino acid sequence of SEQ ID NO: 2, 4, 38, or 40, and having an endoglucanase activity, wherein the N-terminal amino acid is pyroglutamic acid.

2. A protein produced by the steps comprising:
   cultivating a host cell transformed with an expression vector comprising a polynucleotide encoding the protein according to claim 1, and recovering the protein from the host cell or culture obtained by the cultivation.

3. A method for suppressing a reduction in an endoglucanase activity in the presence of a surfactant, characterized by modifying a protein having the endoglucanase activity in which the N-terminus is an amino acid other than pyroglutamic acid, to a protein according to claim 1.

4. The method according to claim 3, wherein the modification is carried out by adding pyroglutamic acid or an amino acid convertible into pyroglutamic acid, or a peptide having the N-terminus of pyroglutamic acid or an amino acid convertible into pyroglutamic acid, to the N-terminus of the protein having the endoglucanase activity in which the N-terminus is an amino acid other than pyroglutamic acid.

5. The method according to claim 3, wherein the modification is carried out by substituting pyroglutamic acid or an amino acid convertible into pyroglutamic acid, or a peptide having the N-terminus of pyroglutamic acid or an amino acid convertible into pyroglutamic acid, for the N-terminal amino acid or an N-terminal region of the protein having the endoglucanase activity in which the N-terminus is an amino acid other than pyroglutamic acid.

6. The method according to claim 3, wherein the protein having the endoglucanase activity in which the N-terminus is an amino acid other than pyroglutamic acid is a cellulase belonging to family 45.

7. The method according to 4, wherein the protein having the endoglucanase activity in which the N-terminus is an amino acid other than pyroglutamic acid is a cellulase belonging to family 45.

8. The method according to claim 5, wherein the protein having the endoglucanase activity in which the N-terminus is an amino acid other than pyroglutamic acid is a cellulase belonging to family 45.

* * * * *

SEQUENCE LISTING

```
<160> NUMBER OF SEQ ID NOS: 48

<210> SEQ ID NO 1
<211> LENGTH: 870
<212> TYPE: DNA
<213> ORGANISM: Humicola insolens MN200-1
<220> FEATURE:
<221> NAME/KEY: CDS
<222> LOCATION: (1)..(870)
<220> FEATURE:
<221> NAME/KEY: misc_feature
<222> LOCATION: (1)..(3)
<223> OTHER INFORMATION: Pyroglutamic acid
<220> FEATURE:
<221> NAME/KEY: source
<222> LOCATION: (16)..(870)
<223> OTHER INFORMATION: Humicola insolens MN200-1

<400> SEQUENCE: 1 cag aac tgt gga tcc gct gat ggc aag tcc acc cgc tac tgg gac tgc       48
Gln Asn Cys Gly Ser Ala Asp Gly Lys Ser Thr Arg Tyr Trp Asp Cys
1               5                   10                  15
```

| | | |
|---|---|---|
| tgc aag cct tcg tgc ggc tgg gcc aag aag gct ccc gtg aac cag cct<br>Cys Lys Pro Ser Cys Gly Trp Ala Lys Lys Ala Pro Val Asn Gln Pro<br>20              25                  30 | | 96 |
| gtc ttc tcc tgc aac gcc aac ttc cag cgt ctc act gac ttc gac gcc<br>Val Phe Ser Cys Asn Ala Asn Phe Gln Arg Leu Thr Asp Phe Asp Ala<br>    35                  40                  45 | | 144 |
| aag tcc ggc tgc gag ccg ggt ggt gtc gcc tac tcg tgc gcc gac cag<br>Lys Ser Gly Cys Glu Pro Gly Gly Val Ala Tyr Ser Cys Ala Asp Gln<br>50              55                  60 | | 192 |
| acc cca tgg gct gtg aac gac gac ttc gcg ttc ggt ttt gct gcc acc<br>Thr Pro Trp Ala Val Asn Asp Asp Phe Ala Phe Gly Phe Ala Ala Thr<br>65              70                  75                  80 | | 240 |
| tct att gcc ggc agc aat gag gcg ggc tgg tgc tgc gcc tgc tac gag<br>Ser Ile Ala Gly Ser Asn Glu Ala Gly Trp Cys Cys Ala Cys Tyr Glu<br>    85                  90                  95 | | 288 |
| ctc acc ttc aca tcc ggt cct gtt gct ggc aag aag atg gtc gtc cag<br>Leu Thr Phe Thr Ser Gly Pro Val Ala Gly Lys Lys Met Val Val Gln<br>100                 105                 110 | | 336 |
| tcc acc agc act ggc ggt gat ctt ggc agc aac cac ttc gat ctc aac<br>Ser Thr Ser Thr Gly Gly Asp Leu Gly Ser Asn His Phe Asp Leu Asn<br>    115                 120                 125 | | 384 |
| atc ccc ggc ggc ggc gtc ggc atc ttc gac gga tgc act ccc cag ttc<br>Ile Pro Gly Gly Gly Val Gly Ile Phe Asp Gly Cys Thr Pro Gln Phe<br>130                 135                 140 | | 432 |
| ggc ggt ctg ccc ggc cag cgc tac ggc ggc atc tcg tcc cgc aac gag<br>Gly Gly Leu Pro Gly Gln Arg Tyr Gly Gly Ile Ser Ser Arg Asn Glu<br>145                 150                 155                 160 | | 480 |
| tgc gat cgg ttc ccc gac gcc ctc aag ccc ggc tgc tac tgg cgc ttc<br>Cys Asp Arg Phe Pro Asp Ala Leu Lys Pro Gly Cys Tyr Trp Arg Phe<br>            165                 170                 175 | | 528 |
| gac tgg ttc aag aac gcc gac aac ccg agc ttc agc ttc cgt cag gtc<br>Asp Trp Phe Lys Asn Ala Asp Asn Pro Ser Phe Ser Phe Arg Gln Val<br>        180                 185                 190 | | 576 |
| caa tgc cca gcc gag ctc gtc gct cgc acc gga tgc cgc cgc aac gac<br>Gln Cys Pro Ala Glu Leu Val Ala Arg Thr Gly Cys Arg Arg Asn Asp<br>    195                 200                 205 | | 624 |
| gac ggc aac ttc cct gcc gtc cag atc ccc tcc agc agc acc agc tct<br>Asp Gly Asn Phe Pro Ala Val Gln Ile Pro Ser Ser Ser Thr Ser Ser<br>210                 215                 220 | | 672 |
| ccg gtc ggc cag cct acc agt acc agc acc acc tcc acc tcc acc acc<br>Pro Val Gly Gln Pro Thr Ser Thr Ser Thr Thr Ser Thr Ser Thr Thr<br>225                 230                 235                 240 | | 720 |
| tcg agc ccg ccc gtc cag cct acg act ccc agc ggc tgc act gct gag<br>Ser Ser Pro Pro Val Gln Pro Thr Thr Pro Ser Gly Cys Thr Ala Glu<br>            245                 250                 255 | | 768 |
| agg tgg gct cag tgc ggc ggc aat ggc tgg agc ggc tgc acc acc tgc<br>Arg Trp Ala Gln Cys Gly Gly Asn Gly Trp Ser Gly Cys Thr Thr Cys<br>        260                 265                 270 | | 816 |
| gtc gct ggc agc acc tgc acg aag att aat gac tgg tac cat cag tgc<br>Val Ala Gly Ser Thr Cys Thr Lys Ile Asn Asp Trp Tyr His Gln Cys<br>    275                 280                 285 | | 864 |
| ctg taa<br>Leu | | 870 |

<210> SEQ ID NO 2
<211> LENGTH: 289
<212> TYPE: PRT
<213> ORGANISM: Humicola insolens MN200-1
<220> FEATURE:
<221> NAME/KEY: misc_feature
<222> LOCATION: (1)..(3)
<223> OTHER INFORMATION: Pyroglutamic acid

<400> SEQUENCE: 2

```
Gln Asn Cys Gly Ser Ala Asp Gly Lys Ser Thr Arg Tyr Trp Asp Cys
1               5                   10                  15
Cys Lys Pro Ser Cys Gly Trp Ala Lys Lys Ala Pro Val Asn Gln Pro
            20                  25                  30
Val Phe Ser Cys Asn Ala Asn Phe Gln Arg Leu Thr Asp Phe Asp Ala
        35                  40                  45
Lys Ser Gly Cys Glu Pro Gly Val Ala Tyr Ser Cys Ala Asp Gln
    50                  55                  60
Thr Pro Trp Ala Val Asn Asp Asp Phe Ala Phe Gly Phe Ala Ala Thr
65                  70                  75                  80
Ser Ile Ala Gly Ser Asn Glu Ala Gly Trp Cys Cys Ala Cys Tyr Glu
                85                  90                  95
Leu Thr Phe Thr Ser Gly Pro Val Ala Gly Lys Lys Met Val Val Gln
            100                 105                 110
Ser Thr Ser Thr Gly Gly Asp Leu Gly Ser Asn His Phe Asp Leu Asn
        115                 120                 125
Ile Pro Gly Gly Gly Val Gly Ile Phe Asp Gly Cys Thr Pro Gln Phe
130                 135                 140
Gly Gly Leu Pro Gly Gln Arg Tyr Gly Gly Ile Ser Ser Arg Asn Glu
145                 150                 155                 160
Cys Asp Arg Phe Pro Asp Ala Leu Lys Pro Gly Cys Tyr Trp Arg Phe
                165                 170                 175
Asp Trp Phe Lys Asn Ala Asp Asn Pro Ser Phe Ser Phe Arg Gln Val
            180                 185                 190
Gln Cys Pro Ala Glu Leu Val Ala Arg Thr Gly Cys Arg Arg Asn Asp
        195                 200                 205
Asp Gly Asn Phe Pro Ala Val Gln Ile Pro Ser Ser Ser Thr Ser Ser
    210                 215                 220
Pro Val Gly Gln Pro Thr Ser Thr Ser Thr Ser Thr Ser Thr Thr
225                 230                 235                 240
Ser Ser Pro Pro Val Gln Pro Thr Thr Pro Ser Gly Cys Thr Ala Glu
                245                 250                 255
Arg Trp Ala Gln Cys Gly Gly Asn Gly Trp Ser Gly Cys Thr Thr Cys
            260                 265                 270
Val Ala Gly Ser Thr Cys Thr Lys Ile Asn Asp Trp Tyr His Gln Cys
        275                 280                 285
Leu
```

<210> SEQ ID NO 3
<211> LENGTH: 897
<212> TYPE: DNA
<213> ORGANISM: Staphylotrichum coccosporum IFO 31817
<220> FEATURE:
<221> NAME/KEY: CDS
<222> LOCATION: (1)..(897)
<220> FEATURE:
<221> NAME/KEY: misc_feature
<222> LOCATION: (1)..(3)
<223> OTHER INFORMATION: Pyroglutamic acid
<220> FEATURE:
<221> NAME/KEY: source
<222> LOCATION: (13)..(897)
<223> OTHER INFORMATION: Staphylotrichum coccosporum IFO 31817

<400> SEQUENCE: 3

```
cag tcg gca tgc gat ggc aag tcc acc cgc tac tgg gac tgc tgc aag       48
Gln Ser Ala Cys Asp Gly Lys Ser Thr Arg Tyr Trp Asp Cys Cys Lys
```

|  |  |  |
|---|---|---|
| cct tcg tgc tcg tgg ccc ggc aag gcc tcg gtg aac cag ccc gtc ttc<br>Pro Ser Cys Ser Trp Pro Gly Lys Ala Ser Val Asn Gln Pro Val Phe<br>20 25 30 | | 96 |
| gcc tgc agc gcc aac ttc cag cgc atc agc gac ccc aac gtc aag tcg<br>Ala Cys Ser Ala Asn Phe Gln Arg Ile Ser Asp Pro Asn Val Lys Ser<br>35 40 45 | | 144 |
| ggc tgc gac ggc ggc tcc gcc tac gcc tgc gcc gac cag acc ccg tgg<br>Gly Cys Asp Gly Gly Ser Ala Tyr Ala Cys Ala Asp Gln Thr Pro Trp<br>50 55 60 | | 192 |
| gcc gtc aac gac aac ttc tcg tac ggc ttc gcc gcc acg tcc atc tcg<br>Ala Val Asn Asp Asn Phe Ser Tyr Gly Phe Ala Ala Thr Ser Ile Ser<br>65 70 75 80 | | 240 |
| ggc ggc aac gag gcc tcg tgg tgc tgt ggc tgc tac gag ctg acc ttc<br>Gly Gly Asn Glu Ala Ser Trp Cys Cys Gly Cys Tyr Glu Leu Thr Phe<br>85 90 95 | | 288 |
| acc tcg ggc ccc gtc gct ggc aag acc atg gtt gtc cag tcc acc tcg<br>Thr Ser Gly Pro Val Ala Gly Lys Thr Met Val Val Gln Ser Thr Ser<br>100 105 110 | | 336 |
| acc ggc ggc gac ctc ggc acc aac cac ttc gac ctg gcc atg ccc ggt<br>Thr Gly Gly Asp Leu Gly Thr Asn His Phe Asp Leu Ala Met Pro Gly<br>115 120 125 | | 384 |
| ggt ggt gtc ggc atc ttc gac ggc tgc tcg ccc cag ttc ggc ggc ctc<br>Gly Gly Val Gly Ile Phe Asp Gly Cys Ser Pro Gln Phe Gly Gly Leu<br>130 135 140 | | 432 |
| gcc ggc gac cgc tac ggc ggc gtc tcg tcg cgc agc cag tgc gac tcg<br>Ala Gly Asp Arg Tyr Gly Gly Val Ser Ser Arg Ser Gln Cys Asp Ser<br>145 150 155 160 | | 480 |
| ttc ccc gcc gcc ctc aag ccc ggc tgc tac tgg cgc ttc gac tgg ttc<br>Phe Pro Ala Ala Leu Lys Pro Gly Cys Tyr Trp Arg Phe Asp Trp Phe<br>165 170 175 | | 528 |
| aag aac gcc gac aac ccg acc ttc acc ttc cgc cag gtc cag tgc ccg<br>Lys Asn Ala Asp Asn Pro Thr Phe Thr Phe Arg Gln Val Gln Cys Pro<br>180 185 190 | | 576 |
| tcg gag ctc gtc gcc cgc acc ggc tgc cgc cgc aac gac gac ggc aac<br>Ser Glu Leu Val Ala Arg Thr Gly Cys Arg Arg Asn Asp Asp Gly Asn<br>195 200 205 | | 624 |
| ttc ccc gtc ttc acc cct ccc tcg ggc ggt cag tcc tcc tcg tct tcc<br>Phe Pro Val Phe Thr Pro Pro Ser Gly Gly Gln Ser Ser Ser Ser Ser<br>210 215 220 | | 672 |
| tcc tcc agc agc gcc aag ccc acc tcc acc tcc acc tcg acc acc tcc<br>Ser Ser Ser Ser Ala Lys Pro Thr Ser Thr Ser Thr Ser Thr Thr Ser<br>225 230 235 240 | | 720 |
| acc aag gct acc tcc acc acc tcg acc gcc tcc agc cag acc tcg tcg<br>Thr Lys Ala Thr Ser Thr Thr Ser Thr Ala Ser Ser Gln Thr Ser Ser<br>245 250 255 | | 768 |
| tcc acc ggc ggc ggc tgc gcc gcc cag cgc tgg gcg cag tgc ggc ggc<br>Ser Thr Gly Gly Gly Cys Ala Ala Gln Arg Trp Ala Gln Cys Gly Gly<br>260 265 270 | | 816 |
| atc ggg ttc tcg ggc tgc acc acg tgc gtc agc ggc acc acc tgc aac<br>Ile Gly Phe Ser Gly Cys Thr Thr Cys Val Ser Gly Thr Thr Cys Asn<br>275 280 285 | | 864 |
| aag cag aac gac tgg tac tcg cag tgc ctt taa<br>Lys Gln Asn Asp Trp Tyr Ser Gln Cys Leu<br>290 295 | | 897 |

<210> SEQ ID NO 4
<211> LENGTH: 298
<212> TYPE: PRT
<213> ORGANISM: Staphylotrichum coccosporum IFO 31817
<220> FEATURE:

<221> NAME/KEY: misc_feature
<222> LOCATION: (1)..(3)
<223> OTHER INFORMATION: Pyroglutamic acid

<400> SEQUENCE: 4

| Gln | Ser | Ala | Cys | Asp | Gly | Lys | Ser | Thr | Arg | Tyr | Trp | Asp | Cys | Cys | Lys |
|---|---|---|---|---|---|---|---|---|---|---|---|---|---|---|---|
| 1 | | | | 5 | | | | | 10 | | | | | 15 | |

| Pro | Ser | Cys | Ser | Trp | Pro | Gly | Lys | Ala | Ser | Val | Asn | Gln | Pro | Val | Phe |
|---|---|---|---|---|---|---|---|---|---|---|---|---|---|---|---|
| | | | 20 | | | | | 25 | | | | | 30 | | |

| Ala | Cys | Ser | Ala | Asn | Phe | Gln | Arg | Ile | Ser | Asp | Pro | Asn | Val | Lys | Ser |
|---|---|---|---|---|---|---|---|---|---|---|---|---|---|---|---|
| | | 35 | | | | | 40 | | | | | 45 | | | |

| Gly | Cys | Asp | Gly | Gly | Ser | Ala | Tyr | Ala | Cys | Ala | Asp | Gly | Thr | Pro | Trp |
|---|---|---|---|---|---|---|---|---|---|---|---|---|---|---|---|
| | 50 | | | | | 55 | | | | | 60 | | | | |

| Ala | Val | Asn | Asp | Asn | Phe | Ser | Tyr | Gly | Phe | Ala | Ala | Thr | Ser | Ile | Ser |
|---|---|---|---|---|---|---|---|---|---|---|---|---|---|---|---|
| 65 | | | | | 70 | | | | | 75 | | | | | 80 |

| Gly | Gly | Asn | Glu | Ala | Ser | Trp | Cys | Cys | Gly | Cys | Tyr | Glu | Leu | Thr | Phe |
|---|---|---|---|---|---|---|---|---|---|---|---|---|---|---|---|
| | | | | 85 | | | | | 90 | | | | | 95 | |

| Thr | Ser | Gly | Pro | Val | Ala | Gly | Lys | Thr | Met | Val | Val | Gln | Ser | Thr | Ser |
|---|---|---|---|---|---|---|---|---|---|---|---|---|---|---|---|
| | | | 100 | | | | | 105 | | | | | 110 | | |

| Thr | Gly | Gly | Asp | Leu | Gly | Thr | Asn | His | Phe | Asp | Leu | Ala | Met | Pro | Gly |
|---|---|---|---|---|---|---|---|---|---|---|---|---|---|---|---|
| | | 115 | | | | | 120 | | | | | 125 | | | |

| Gly | Gly | Val | Gly | Ile | Phe | Asp | Gly | Cys | Ser | Pro | Gln | Phe | Gly | Gly | Leu |
|---|---|---|---|---|---|---|---|---|---|---|---|---|---|---|---|
| | 130 | | | | | 135 | | | | | 140 | | | | |

| Ala | Gly | Asp | Arg | Tyr | Gly | Gly | Val | Ser | Ser | Arg | Ser | Gln | Cys | Asp | Ser |
|---|---|---|---|---|---|---|---|---|---|---|---|---|---|---|---|
| 145 | | | | | 150 | | | | | 155 | | | | | 160 |

| Phe | Pro | Ala | Ala | Leu | Lys | Pro | Gly | Cys | Tyr | Trp | Arg | Phe | Asp | Trp | Phe |
|---|---|---|---|---|---|---|---|---|---|---|---|---|---|---|---|
| | | | | 165 | | | | | 170 | | | | | 175 | |

| Lys | Asn | Ala | Asp | Asn | Pro | Thr | Phe | Thr | Phe | Arg | Gln | Val | Gln | Cys | Pro |
|---|---|---|---|---|---|---|---|---|---|---|---|---|---|---|---|
| | | 180 | | | | | 185 | | | | | 190 | | | |

| Ser | Glu | Leu | Val | Ala | Arg | Thr | Gly | Cys | Arg | Arg | Asn | Asp | Asp | Gly | Asn |
|---|---|---|---|---|---|---|---|---|---|---|---|---|---|---|---|
| | | 195 | | | | | 200 | | | | | 205 | | | |

| Phe | Pro | Val | Phe | Thr | Pro | Pro | Ser | Gly | Gly | Gln | Ser | Ser | Ser | Ser | Ser |
|---|---|---|---|---|---|---|---|---|---|---|---|---|---|---|---|
| 210 | | | | | 215 | | | | | 220 | | | | | |

| Ser | Ser | Ser | Ser | Ala | Lys | Pro | Thr | Ser | Thr | Ser | Thr | Thr | Thr | Thr | Ser |
|---|---|---|---|---|---|---|---|---|---|---|---|---|---|---|---|
| 225 | | | | | 230 | | | | | 235 | | | | | 240 |

| Thr | Lys | Ala | Thr | Ser | Thr | Thr | Ser | Thr | Ala | Ser | Ser | Gln | Thr | Ser | Ser |
|---|---|---|---|---|---|---|---|---|---|---|---|---|---|---|---|
| | | | | 245 | | | | | 250 | | | | | 255 | |

| Ser | Thr | Gly | Gly | Gly | Cys | Ala | Ala | Gln | Arg | Trp | Ala | Gln | Cys | Gly | Gly |
|---|---|---|---|---|---|---|---|---|---|---|---|---|---|---|---|
| | | | 260 | | | | | 265 | | | | | 270 | | |

| Ile | Gly | Phe | Ser | Gly | Cys | Thr | Thr | Cys | Val | Ser | Gly | Thr | Thr | Cys | Asn |
|---|---|---|---|---|---|---|---|---|---|---|---|---|---|---|---|
| | | | 275 | | | | | 280 | | | | | 285 | | |

| Lys | Gln | Asn | Asp | Trp | Tyr | Ser | Gln | Cys | Leu |
|---|---|---|---|---|---|---|---|---|---|
| | 290 | | | | | 295 | | | |

```
<210> SEQ ID NO 5
<211> LENGTH: 1037
<212> TYPE: DNA
<213> ORGANISM: Staphylotrichum coccosporum IFO 31817
<220> FEATURE:
<221> NAME/KEY: sig_peptide
<222> LOCATION: (1)..(63)
<220> FEATURE:
<221> NAME/KEY: exon
<222> LOCATION: (64)..(333)
<220> FEATURE:
<221> NAME/KEY: Intron
<222> LOCATION: (334)..(419)
<220> FEATURE:
<221> NAME/KEY: exon
<222> LOCATION: (420)..(1037)
```

<400> SEQUENCE: 5

```
atgcgttcct ccccgtcct ccgcacggcc ctggccgctg ccctcccct ggccgccctc        60
```

| gct | gcc | gat | ggc | aag | tcg | acc | cgc | tac | tgg | gac | tgt | tgc | aag | ccg | tcg | 108 |
|---|---|---|---|---|---|---|---|---|---|---|---|---|---|---|---|---|
| Ala | Asp | Gly | Lys | Ser | Thr | Arg | Tyr | Trp | Asp | Cys | Cys | Lys | Pro | Ser | | |
| 1 | | | | 5 | | | | | 10 | | | | | 15 | | |

| tgc | tcg | tgg | ccc | ggc | aag | gcc | tcg | gtg | aac | cag | ccc | gtc | ttc | gcc | tgc | 156 |
|---|---|---|---|---|---|---|---|---|---|---|---|---|---|---|---|---|
| Cys | Ser | Trp | Pro | Gly | Lys | Ala | Ser | Val | Asn | Gln | Pro | Val | Phe | Ala | Cys | |
| | | | 20 | | | | | 25 | | | | | 30 | | | |

| agc | gcc | aac | ttc | cag | cgc | atc | agc | gac | ccc | aac | gtc | aag | tcg | ggc | tgc | 204 |
|---|---|---|---|---|---|---|---|---|---|---|---|---|---|---|---|---|
| Ser | Ala | Asn | Phe | Gln | Arg | Ile | Ser | Asp | Pro | Asn | Val | Lys | Ser | Gly | Cys | |
| | | 35 | | | | | 40 | | | | | 45 | | | | |

| gac | ggc | ggc | tcc | gcc | tac | gcc | tgc | gcc | gac | cag | acc | ccg | tgg | gcc | gtc | 252 |
|---|---|---|---|---|---|---|---|---|---|---|---|---|---|---|---|---|
| Asp | Gly | Gly | Ser | Ala | Tyr | Ala | Cys | Ala | Asp | Gln | Thr | Pro | Trp | Ala | Val | |
| | 50 | | | | | 55 | | | | | 60 | | | | | |

| aac | gac | aac | ttc | tcg | tac | ggc | ttc | gcc | gcc | acg | tcc | atc | tcg | ggc | ggc | 300 |
|---|---|---|---|---|---|---|---|---|---|---|---|---|---|---|---|---|
| Asn | Asp | Asn | Phe | Ser | Tyr | Gly | Phe | Ala | Ala | Thr | Ser | Ile | Ser | Gly | Gly | |
| 65 | | | | 70 | | | | | 75 | | | | | | | |

| aac | gag | gcc | tcg | tgg | tgc | tgt | ggc | tgc | tac | gag | tgagtgcttc ccccccccc | | | | | 353 |
|---|---|---|---|---|---|---|---|---|---|---|---|---|---|---|---|---|
| Asn | Glu | Ala | Ser | Trp | Cys | Cys | Gly | Cys | Tyr | Glu | | | | | | |
| 80 | | | | | 85 | | | | | 90 | | | | | | |

```
ccccccccac cccggttcg gtcccttgcc gtgccttctt catactaacc gcctaccccc       413
```

| tccagg | ctg | acc | ttc | acc | tcg | ggc | ccc | gtc | gct | ggc | aag | acc | atg | gtt | 461 |
|---|---|---|---|---|---|---|---|---|---|---|---|---|---|---|---|
| | Leu | Thr | Phe | Thr | Ser | Gly | Pro | Val | Ala | Gly | Lys | Thr | Met | Val | |
| | | | | 95 | | | | | 100 | | | | | | |

| gtc | cag | tcc | acc | tcg | acc | ggc | ggc | gac | ctc | ggc | acc | aac | cac | ttc | gac | 509 |
|---|---|---|---|---|---|---|---|---|---|---|---|---|---|---|---|---|
| Val | Gln | Ser | Thr | Ser | Thr | Gly | Gly | Asp | Leu | Gly | Thr | Asn | His | Phe | Asp | |
| 105 | | | | | 110 | | | | | 115 | | | | | 120 | |

| ctg | gcc | atg | ccc | ggt | ggt | ggt | gtc | ggc | atc | ttc | gac | ggc | tgc | tcg | ccc | 557 |
|---|---|---|---|---|---|---|---|---|---|---|---|---|---|---|---|---|
| Leu | Ala | Met | Pro | Gly | Gly | Gly | Val | Gly | Ile | Phe | Asp | Gly | Cys | Ser | Pro | |
| | | | 125 | | | | | 130 | | | | | 135 | | | |

| cag | ttc | ggc | ggc | ctc | gcc | ggc | gac | cgc | tac | ggc | ggc | gtc | tcg | tcg | cgc | 605 |
|---|---|---|---|---|---|---|---|---|---|---|---|---|---|---|---|---|
| Gln | Phe | Gly | Gly | Leu | Ala | Gly | Asp | Arg | Tyr | Gly | Gly | Val | Ser | Ser | Arg | |
| | | 140 | | | | | 145 | | | | | 150 | | | | |

| agc | cag | tgc | gac | tcg | ttc | ccc | gcc | gcc | ctc | aag | ccc | ggc | tgc | tac | tgg | 653 |
|---|---|---|---|---|---|---|---|---|---|---|---|---|---|---|---|---|
| Ser | Gln | Cys | Asp | Ser | Phe | Pro | Ala | Ala | Leu | Lys | Pro | Gly | Cys | Tyr | Trp | |
| | | 155 | | | | | 160 | | | | | 165 | | | | |

| cgc | ttc | gac | tgg | ttc | aag | aac | gcc | gac | aac | ccg | acc | ttc | acc | ttc | cgc | 701 |
|---|---|---|---|---|---|---|---|---|---|---|---|---|---|---|---|---|
| Arg | Phe | Asp | Trp | Phe | Lys | Asn | Ala | Asp | Asn | Pro | Thr | Phe | Thr | Phe | Arg | |
| | 170 | | | | | 175 | | | | | 180 | | | | | |

| cag | gtc | cag | tgc | ccg | tcg | gag | ctc | gtc | gcc | cgc | acc | ggc | tgc | cgc | cgc | 749 |
|---|---|---|---|---|---|---|---|---|---|---|---|---|---|---|---|---|
| Gln | Val | Gln | Cys | Pro | Ser | Glu | Leu | Val | Ala | Arg | Thr | Gly | Cys | Arg | Arg | |
| 185 | | | | | 190 | | | | | 195 | | | | | 200 | |

| aac | gac | gac | ggc | aac | ttc | ccc | gtc | ttc | acc | cct | ccc | tcg | ggc | ggt | cag | 797 |
|---|---|---|---|---|---|---|---|---|---|---|---|---|---|---|---|---|
| Asn | Asp | Asp | Gly | Asn | Phe | Pro | Val | Phe | Thr | Pro | Pro | Ser | Gly | Gly | Gln | |
| | | | | 205 | | | | | 210 | | | | | 215 | | |

| tcc | tcc | tcg | tct | tcc | tcc | tcc | agc | agc | gcc | aag | ccc | acc | tcc | acc | tcc | 845 |
|---|---|---|---|---|---|---|---|---|---|---|---|---|---|---|---|---|
| Ser | Ser | Ser | Ser | Ser | Ser | Ser | Ser | Ala | Lys | Pro | Thr | Ser | Thr | Ser | | |
| | | | 220 | | | | | 225 | | | | | 230 | | | |

| acc | tcg | acc | acc | tcc | acc | aag | gct | acc | tcc | acc | acc | tcg | acc | gcc | tcc | 893 |
|---|---|---|---|---|---|---|---|---|---|---|---|---|---|---|---|---|
| Thr | Ser | Thr | Thr | Ser | Thr | Lys | Ala | Thr | Ser | Thr | Thr | Ser | Thr | Ala | Ser | |
| | | | 235 | | | | | 240 | | | | | 245 | | | |

| agc | cag | acc | tcg | tcg | tcc | acc | ggc | ggc | ggc | tgc | gcc | gcc | cag | cgc | tgg | 941 |
|---|---|---|---|---|---|---|---|---|---|---|---|---|---|---|---|---|
| Ser | Gln | Thr | Ser | Ser | Ser | Thr | Gly | Gly | Gly | Cys | Ala | Ala | Gln | Arg | Trp | |
| | | 250 | | | | | 255 | | | | | 260 | | | | |

| gcg | cag | tgc | ggc | ggc | atc | ggg | ttc | tcg | ggc | tgc | acc | acg | tgc | gtc | agc | 989 |
|---|---|---|---|---|---|---|---|---|---|---|---|---|---|---|---|---|
| Ala | Gln | Cys | Gly | Gly | Ile | Gly | Phe | Ser | Gly | Cys | Thr | Thr | Cys | Val | Ser | |
| 265 | | | | | 270 | | | | | 275 | | | | | 280 | |

| ggc | acc | acc | tgc | aac | aag | cag | aac | gac | tgg | tac | tcg | cag | tgc | ctt | tga | 1037 |
|---|---|---|---|---|---|---|---|---|---|---|---|---|---|---|---|---|

Gly Thr Thr Cys Asn Lys Gln Asn Asp Trp Tyr Ser Gln Cys Leu
            285                 290                 295

```
<210> SEQ ID NO 6
<211> LENGTH: 36
<212> TYPE: DNA
<213> ORGANISM: Artificial Sequence
<220> FEATURE:
<223> OTHER INFORMATION: Chemcially synthesized Primer MNC-02

<400> SEQUENCE: 6
gagcgccaga actgtggatc cacttggtga gcaatg                              36

<210> SEQ ID NO 7
<211> LENGTH: 35
<212> TYPE: DNA
<213> ORGANISM: Artificial Sequence
<220> FEATURE:
<223> OTHER INFORMATION: Chemcially synthesized Primer MNC-03

<400> SEQUENCE: 7
tccgccgttc tgagcggatc caggcgtttg gcgcg                               35

<210> SEQ ID NO 8
<211> LENGTH: 36
<212> TYPE: DNA
<213> ORGANISM: Artificial Sequence
<220> FEATURE:
<223> OTHER INFORMATION: Chemcially synthesized Primer MKA-05

<400> SEQUENCE: 8
gccgcccagc aggcgggatc cctcaccacc gagagg                              36

<210> SEQ ID NO 9
<211> LENGTH: 36
<212> TYPE: DNA
<213> ORGANISM: Artificial Sequence
<220> FEATURE:
<223> OTHER INFORMATION: Chemcially synthesized Primer MKA-06

<400> SEQUENCE: 9
tgatcgtcga gtcagggatc cagaatttac aggcac                              36

<210> SEQ ID NO 10
<211> LENGTH: 44
<212> TYPE: DNA
<213> ORGANISM: Artificial Sequence
<220> FEATURE:
<223> OTHER INFORMATION: Chemcially synthesized plasmid pMKD01
<220> FEATURE:
<221> NAME/KEY: misc_feature
<222> LOCATION: (24)..(25)
<223> OTHER INFORMATION: non-consecutive bases

<400> SEQUENCE: 10
gagcgccaga actgtggatc cctctgcctg taagcggatc cagg                     44

<210> SEQ ID NO 11
<211> LENGTH: 10
<212> TYPE: PRT
<213> ORGANISM: Artificial Sequence
<220> FEATURE:
<223> OTHER INFORMATION: Chemcially synthesized plasmid pMKD01
<220> FEATURE:
<221> NAME/KEY: NON_CONS
<222> LOCATION: (8)..(9)
<220> FEATURE:
<221> NAME/KEY: MOD_RES
<222> LOCATION: (1)..(1)
```

-continued

<223> OTHER INFORMATION: PYRROLIDONE CARBOXYLIC ACID

<400> SEQUENCE: 11

Glu Arg Gln Asn Cys Gly Ser Leu Cys Leu
1               5                   10

<210> SEQ ID NO 12
<211> LENGTH: 53
<212> TYPE: DNA
<213> ORGANISM: Artificial Sequence
<220> FEATURE:
<223> OTHER INFORMATION: Chemcially synthesized Primer pMN-Bam

<400> SEQUENCE: 12
ggtcaaacaa gtctgtgcgg atcctgggac aagatggcca agttcttcct tac        53

<210> SEQ ID NO 13
<211> LENGTH: 44
<212> TYPE: DNA
<213> ORGANISM: Artificial Sequence
<220> FEATURE:
<223> OTHER INFORMATION: Chemcially synthesized plasmid pJD01
<220> FEATURE:
<221> NAME/KEY: misc_feature
<222> LOCATION: (24)..(25)
<223> OTHER INFORMATION: non-consecutive bases

<400> SEQUENCE: 13
tgcggatcct gggacaagat ggccccgttc tgagcggatc cagg                  44

<210> SEQ ID NO 14
<211> LENGTH: 4
<212> TYPE: PRT
<213> ORGANISM: Artificial Sequence
<220> FEATURE:
<223> OTHER INFORMATION: Chemcially synthesized plasmid pJD01
<220> FEATURE:
<221> NAME/KEY: NON_CONS
<222> LOCATION: (2)..(3)

<400> SEQUENCE: 14

Met Ala Pro Phe
1

<210> SEQ ID NO 15
<211> LENGTH: 37
<212> TYPE: DNA
<213> ORGANISM: Artificial Sequence
<220> FEATURE:
<223> OTHER INFORMATION: Chemcially synthesized Primer NCE4-Ne

<400> SEQUENCE: 15 gggggatcc tgggacaaga tgcgttcctc ccctctc                           37

<210> SEQ ID NO 16
<211> LENGTH: 32
<212> TYPE: DNA
<213> ORGANISM: Artificial Sequence
<220> FEATURE:
<223> OTHER INFORMATION: Chemcially synthesized Primer NCE4-Ce

<400> SEQUENCE: 16 gggggatcc ctgcgtttac aggcactgat gg                                32

<210> SEQ ID NO 17
<211> LENGTH: 30
<212> TYPE: DNA
<213> ORGANISM: Artificial Sequence

```
<220> FEATURE:
<223> OTHER INFORMATION: Chemcially synthesized Primer NCE4-Ns

<400> SEQUENCE: 17
ccggtgttgg ccggatccgc tgatggcaag                                              30

<210> SEQ ID NO 18
<211> LENGTH: 30
<212> TYPE: DNA
<213> ORGANISM: Artificial Sequence
<220> FEATURE:
<223> OTHER INFORMATION: Chemcially synthesized Primer NCE4-Cs

<400> SEQUENCE: 18
taaggccctc aaggatccct gcgtctacag                                              30

<210> SEQ ID NO 19
<211> LENGTH: 7
<212> TYPE: PRT
<213> ORGANISM: Humicola insolens MN200-1

<400> SEQUENCE: 19

Ala Asp Gly Lys Ser Thr Arg
1               5

<210> SEQ ID NO 20
<211> LENGTH: 12
<212> TYPE: PRT
<213> ORGANISM: Humicola insolens MN200-1
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MUTAGEN
<222> LOCATION: (1)..(5)

<400> SEQUENCE: 20

Gln Asn Cys Gly Ser Ala Asp Gly Lys Ser Thr Arg
1               5                   10

<210> SEQ ID NO 21
<211> LENGTH: 36
<212> TYPE: DNA
<213> ORGANISM: Artificial Sequence
<220> FEATURE:
<223> OTHER INFORMATION: Chemcially synthesized Primer CBn-Stu

<400> SEQUENCE: 21
gatacatgat gcgcaggcct tagtcgacta gaatgc                                       36

<210> SEQ ID NO 22
<211> LENGTH: 36
<212> TYPE: DNA
<213> ORGANISM: Artificial Sequence
<220> FEATURE:
<223> OTHER INFORMATION: Chemcially synthesized Primer CBc-Xho

<400> SEQUENCE: 22
gatcctcaag cttttgctcg agtaccttac aagcac                                       36

<210> SEQ ID NO 23
<211> LENGTH: 35
<212> TYPE: DNA
<213> ORGANISM: Artificial Sequence
<220> FEATURE:
<223> OTHER INFORMATION: Chemcially synthesized Primer CB1-SmSph
```

<400> SEQUENCE: 23
ggagggtgca tgccgactga gcccgggcag tagcc    35

<210> SEQ ID NO 24
<211> LENGTH: 23
<212> TYPE: DNA
<213> ORGANISM: Artificial Sequence
<220> FEATURE:
<223> OTHER INFORMATION: Chemcially synthesized Primer CB1-Bam

<400> SEQUENCE: 24
gccgggagag gatccagtgg agg    23

<210> SEQ ID NO 25
<211> LENGTH: 30
<212> TYPE: DNA
<213> ORGANISM: Artificial Sequence
<220> FEATURE:
<223> OTHER INFORMATION: Chemcially synthesized Primer CB1-Pst

<400> SEQUENCE: 25
gctcgagtac cttactgcag gcactgagag    30

<210> SEQ ID NO 26
<211> LENGTH: 66
<212> TYPE: DNA
<213> ORGANISM: Artificial Sequence
<220> FEATURE:
<223> OTHER INFORMATION: Chemcially synthesized pCB1-M2

<400> SEQUENCE: 26
ctagtcgact aaggcctgcg catcatgtat caaaagttgg ccctcatctc ggccttcttg    60
gctact    66

<210> SEQ ID NO 27
<211> LENGTH: 14
<212> TYPE: PRT
<213> ORGANISM: Artificial Sequence
<220> FEATURE:
<223> OTHER INFORMATION: Chemcially synthesized plasmid pCB1-M2

<400> SEQUENCE: 27

Met Tyr Gln Lys Leu Ala Leu Ile Ser Ala Phe Leu Ala Thr
1               5                   10

<210> SEQ ID NO 28
<211> LENGTH: 61
<212> TYPE: DNA
<213> ORGANISM: Artificial Sequence
<220> FEATURE:
<223> OTHER INFORMATION: Chemcially synthesized plasmid pCB1-M2
<220> FEATURE:
<221> NAME/KEY: misc_feature
<222> LOCATION: (24)..(25)
<223> OTHER INFORMATION: non-consecutive bases

<400> SEQUENCE: 28
gcccgggctc agtcggcatg cacccagtgc ctgcagtaag gtactcgagc aaaagcttga    60
g    61

<210> SEQ ID NO 29
<211> LENGTH: 12
<212> TYPE: PRT
<213> ORGANISM: Artificial Sequence
<220> FEATURE:
<223> OTHER INFORMATION: Chemcially synthesized plasmid pCB1-M2

```
<220> FEATURE:
<221> NAME/KEY: NON_CONS
<222> LOCATION: (8)..(9)

<400> SEQUENCE: 29

Ala Arg Ala Gln Ser Ala Cys Thr Gln Cys Leu Gln
1               5                   10

<210> SEQ ID NO 30
<211> LENGTH: 37
<212> TYPE: DNA
<213> ORGANISM: Artificial Sequence
<220> FEATURE:
<223> OTHER INFORMATION: Chemcially synthesized Primer STCE1-TNERV

<400> SEQUENCE: 30 gggatatcg cgcatcatgc gttcctcccc cgtcctc                           37

<210> SEQ ID NO 31
<211> LENGTH: 33
<212> TYPE: DNA
<213> ORGANISM: Artificial Sequence
<220> FEATURE:
<223> OTHER INFORMATION: Chemcially synthesized Primer STCE1-TCET22I

<400> SEQUENCE: 31
gggatgcatt taaaggcact gcgagtacca gtc                              33

<210> SEQ ID NO 32
<211> LENGTH: 30
<212> TYPE: DNA
<213> ORGANISM: Artificial Sequence
<220> FEATURE:
<223> OTHER INFORMATION: Chemcially synthesized Primer STCE1-TmNSph

<400> SEQUENCE: 32
ggggcatgcg atggcaagtc gacccgctac                                  30

<210> SEQ ID NO 33
<211> LENGTH: 7
<212> TYPE: PRT
<213> ORGANISM: Staphylotrichum coccosporum IFO 31817

<400> SEQUENCE: 33

Ala Asp Gly Lys Ser Thr Arg
1               5

<210> SEQ ID NO 34
<211> LENGTH: 10
<212> TYPE: PRT
<213> ORGANISM: Staphylotrichum coccosporum IFO 31817
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MUTAGEN
<222> LOCATION: (1)..(4)

<400> SEQUENCE: 34

Gln Ser Ala Cys Asp Gly Lys Ser Thr Arg
1               5                   10

<210> SEQ ID NO 35
<211> LENGTH: 33
<212> TYPE: DNA
<213> ORGANISM: Artificial Sequence
<220> FEATURE:
```

-continued

```
<223> OTHER INFORMATION: Chemcially synthesized Primer STCE1-TmNSma

<400> SEQUENCE: 35
ggcccgggct caggccgatg gcaagtcgac ccg                                    33

<210> SEQ ID NO 36
<211> LENGTH: 29
<212> TYPE: DNA
<213> ORGANISM: Artificial Sequence
<220> FEATURE:
<223> OTHER INFORMATION: Chemcially synthesized Primer STCE1-TmNSph-2

<400> SEQUENCE: 36
gggcatgcgc cgatggcaag tcgacccgc                                         29

<210> SEQ ID NO 37
<211> LENGTH: 891
<212> TYPE: DNA
<213> ORGANISM: Staphylotrichum coccosporum IFO 31817
<220> FEATURE:
<221> NAME/KEY: CDS
<222> LOCATION: (1)..(891)
<220> FEATURE:
<221> NAME/KEY: misc_feature
<222> LOCATION: (1)..(3)
<223> OTHER INFORMATION: Pyroglutamic acid
<220> FEATURE:
<221> NAME/KEY: source
<222> LOCATION: (4)..(891)
<223> OTHER INFORMATION: Staphylotrichum coccosporum IFO 31817

<400> SEQUENCE: 37 cag gcc gat ggc aag tcc acc cgc tac tgg gac tgc tgc aag cct tcg        48
Gln Ala Asp Gly Lys Ser Thr Arg Tyr Trp Asp Cys Cys Lys Pro Ser
1               5                   10                  15 tgc tcg tgg ccc ggc aag gcc tcg gtg aac cag ccc gtc ttc gcc tgc        96
Cys Ser Trp Pro Gly Lys Ala Ser Val Asn Gln Pro Val Phe Ala Cys
                20                  25                  30 agc gcc aac ttc cag cgc atc agc gac ccc aac gtc aag tcg ggc tgc       144
Ser Ala Asn Phe Gln Arg Ile Ser Asp Pro Asn Val Lys Ser Gly Cys
            35                  40                  45 gac ggc ggc tcc gcc tac gcc tgc gcc gac cag acc ccg tgg gcc gtc       192
Asp Gly Gly Ser Ala Tyr Ala Cys Ala Asp Gln Thr Pro Trp Ala Val
        50                  55                  60 aac gac aac ttc tcg tac ggc ttc gcc gcc acg tcc atc tcg ggc ggc       240
Asn Asp Asn Phe Ser Tyr Gly Phe Ala Ala Thr Ser Ile Ser Gly Gly
65                  70                  75                  80 aac gag gcc tcg tgg tgc tgt ggc tgc tac gag ctg acc ttc acc tcg       288
Asn Glu Ala Ser Trp Cys Cys Gly Cys Tyr Glu Leu Thr Phe Thr Ser
                85                  90                  95 ggc ccc gtc gct ggc aag acc atg gtt gtc cag tcc acc tcg acc ggc       336
Gly Pro Val Ala Gly Lys Thr Met Val Val Gln Ser Thr Ser Thr Gly
            100                 105                 110 ggc gac ctc ggc acc aac cac ttc gac ctg gcc atg ccc ggt ggt ggt       384
Gly Asp Leu Gly Thr Asn His Phe Asp Leu Ala Met Pro Gly Gly Gly
        115                 120                 125 gtc ggc atc ttc gac ggc tgc tcg ccc cag ttc ggc ggc ctc gcc ggc       432
Val Gly Ile Phe Asp Gly Cys Ser Pro Gln Phe Gly Gly Leu Ala Gly
    130                 135                 140 gac cgc tac ggc ggc gtc tcg tcg cgc agc cag tgc gac tcg ttc ccc       480
Asp Arg Tyr Gly Gly Val Ser Ser Arg Ser Gln Cys Asp Ser Phe Pro
145                 150                 155                 160 gcc gcc ctc aag ccc ggc tgc tac tgg cgc ttc gac tgg ttc aag aac       528
Ala Ala Leu Lys Pro Gly Cys Tyr Trp Arg Phe Asp Trp Phe Lys Asn
                165                 170                 175
```

```
gcc gac aac ccg acc ttc acc ttc cgc cag gtc cag tgc ccg tcg gag      576
Ala Asp Asn Pro Thr Phe Thr Phe Arg Gln Val Gln Cys Pro Ser Glu
        180                 185                 190 ctc gtc gcc cgc acc ggc tgc cgc cgc aac gac gac ggc aac ttc ccc      624
Leu Val Ala Arg Thr Gly Cys Arg Arg Asn Asp Asp Gly Asn Phe Pro
            195                 200                 205 gtc ttc acc cct ccc tcg ggc ggt cag tcc tcc tcg tct tcc tcc tcc      672
Val Phe Thr Pro Pro Ser Gly Gly Gln Ser Ser Ser Ser Ser Ser Ser
210                 215                 220 agc agc gcc aag ccc acc tcc acc tcc acc tcg acc acc tcc acc aag      720
Ser Ser Ala Lys Pro Thr Ser Thr Ser Thr Ser Thr Thr Ser Thr Lys
225                 230                 235                 240 gct acc tcc acc acc tcg acc gcc tcc agc cag acc tcg tcg tcc acc      768
Ala Thr Ser Thr Thr Ser Thr Ala Ser Ser Gln Thr Ser Ser Ser Thr
                245                 250                 255 ggc ggc ggc tgc gcc gcc cag cgc tgg gcg cag tgc ggc ggc atc ggg      816
Gly Gly Gly Cys Ala Ala Gln Arg Trp Ala Gln Cys Gly Gly Ile Gly
            260                 265                 270 ttc tcg ggc tgc acc acg tgc gtc agc ggc acc acc tgc aac aag cag      864
Phe Ser Gly Cys Thr Thr Cys Val Ser Gly Thr Thr Cys Asn Lys Gln
        275                 280                 285 aac gac tgg tac tcg cag tgc ctt taa                                  891
Asn Asp Trp Tyr Ser Gln Cys Leu
    290                 295

<210> SEQ ID NO 38
<211> LENGTH: 296
<212> TYPE: PRT
<213> ORGANISM: Staphylotrichum coccosporum IFO 31817
<220> FEATURE:
<221> NAME/KEY: misc_feature
<222> LOCATION: (1)..(3)
<223> OTHER INFORMATION: Pyroglutamic acid

<400> SEQUENCE: 38

Gln Ala Asp Gly Lys Ser Thr Arg Tyr Trp Asp Cys Cys Lys Pro Ser
1               5                   10                  15

Cys Ser Trp Pro Gly Lys Ala Ser Val Asn Gln Pro Val Phe Ala Cys
            20                  25                  30

Ser Ala Asn Phe Gln Arg Ile Ser Asp Pro Asn Val Lys Ser Gly Cys
        35                  40                  45

Asp Gly Gly Ser Ala Tyr Ala Cys Ala Asp Gln Thr Pro Trp Ala Val
    50                  55                  60

Asn Asp Asn Phe Ser Tyr Gly Phe Ala Ala Thr Ser Ile Ser Gly Gly
65                  70                  75                  80

Asn Glu Ala Ser Trp Cys Cys Gly Cys Tyr Glu Leu Thr Phe Thr Ser
                85                  90                  95

Gly Pro Val Ala Gly Lys Thr Met Val Val Gln Ser Thr Ser Thr Gly
            100                 105                 110

Gly Asp Leu Gly Thr Asn His Phe Asp Leu Ala Met Pro Gly Gly Gly
        115                 120                 125

Val Gly Ile Phe Asp Gly Cys Ser Pro Gln Phe Gly Gly Leu Ala Gly
    130                 135                 140

Asp Arg Tyr Gly Gly Val Ser Ser Arg Ser Gln Cys Asp Ser Phe Pro
145                 150                 155                 160

Ala Ala Leu Lys Pro Gly Cys Tyr Trp Arg Phe Asp Trp Phe Lys Asn
                165                 170                 175

Ala Asp Asn Pro Thr Phe Thr Phe Arg Gln Val Gln Cys Pro Ser Glu
            180                 185                 190
```

```
Leu Val Ala Arg Thr Gly Cys Arg Arg Asn Asp Asp Gly Asn Phe Pro
        195                 200                 205

Val Phe Thr Pro Pro Ser Gly Gln Ser Ser Ser Ser Ser Ser Ser Ser
    210                 215                 220

Ser Ser Ala Lys Pro Thr Ser Thr Ser Thr Ser Thr Ser Thr Ser Lys
225                 230                 235                 240

Ala Thr Ser Thr Thr Ser Thr Ala Ser Ser Gln Thr Ser Ser Ser Thr
                245                 250                 255

Gly Gly Gly Cys Ala Ala Gln Arg Trp Ala Gln Cys Gly Gly Ile Gly
            260                 265                 270

Phe Ser Gly Cys Thr Thr Cys Val Ser Gly Thr Thr Cys Asn Lys Gln
        275                 280                 285

Asn Asp Trp Tyr Ser Gln Cys Leu
        290                 295

<210> SEQ ID NO 39
<211> LENGTH: 900
<212> TYPE: DNA
<213> ORGANISM: Staphylotrichum coccosporum IFO 31817
<220> FEATURE:
<221> NAME/KEY: CDS
<222> LOCATION: (1)..(900)
<220> FEATURE:
<221> NAME/KEY: source
<222> LOCATION: (13)..(900)
<223> OTHER INFORMATION: Pyroglutamic acid
<220> FEATURE:
<221> NAME/KEY: misc_feature
<222> LOCATION: (1)..(3)
<223> OTHER INFORMATION: Pyroglutamic acid

```
tcg ttc ccc gcc gcc ctc aag ccc ggc tgc tac tgg cgc ttc gac tgg        528
Ser Phe Pro Ala Ala Leu Lys Pro Gly Cys Tyr Trp Arg Phe Asp Trp
            165                 170                 175 ttc aag aac gcc gac aac ccg acc ttc acc ttc cgc cag gtc cag tgc        576
Phe Lys Asn Ala Asp Asn Pro Thr Phe Thr Phe Arg Gln Val Gln Cys
        180                 185                 190 ccg tcg gag ctc gtc gcc cgc acc ggc tgc cgc cgc aac gac gac ggc        624
Pro Ser Glu Leu Val Ala Arg Thr Gly Cys Arg Arg Asn Asp Asp Gly
    195                 200                 205 aac ttc ccc gtc ttc acc cct ccc tcg ggc ggt cag tcc tcc tcg tct        672
Asn Phe Pro Val Phe Thr Pro Pro Ser Gly Gly Gln Ser Ser Ser Ser
210                 215                 220 tcc tcc tcc agc agc gcc aag ccc acc tcc acc tcc acc tcg acc acc        720
Ser Ser Ser Ser Ser Ala Lys Pro Thr Ser Thr Ser Thr Ser Thr Thr
225                 230                 235                 240 tcc acc aag gct acc tcc acc acc tcg acc gcc tcc agc cag acc tcg        768
Ser Thr Lys Ala Thr Ser Thr Thr Ser Thr Ala Ser Ser Gln Thr Ser
            245                 250                 255 tcg tcc acc ggc ggc ggc tgc gcc gcc cag cgc tgg gcg cag tgc ggc        816
Ser Ser Thr Gly Gly Gly Cys Ala Ala Gln Arg Trp Ala Gln Cys Gly
        260                 265                 270 ggc atc ggg ttc tcg ggc tgc acc acg tgc gtc agc ggc acc acc tgc        864
Gly Ile Gly Phe Ser Gly Cys Thr Thr Cys Val Ser Gly Thr Thr Cys
    275                 280                 285 aac aag cag aac gac tgg tac tcg cag tgc ctt taa                        900
Asn Lys Gln Asn Asp Trp Tyr Ser Gln Cys Leu
290                 295

<210> SEQ ID NO 40
<211> LENGTH: 299
<212> TYPE: PRT
<213> ORGANISM: Staphylotrichum coccosporum IFO 31817
<220> FEATURE:
<221> NAME/KEY: misc_feature
<222> LOCATION: (1)..(3)
<223> OTHER INFORMATION: Pyroglutamic acid

<400> SEQUENCE: 40

Gln Ser Ala Cys Ala Asp Gly Lys Ser Thr Arg Tyr Trp Asp Cys Cys
1               5                   10                  15

Lys Pro Ser Cys Ser Trp Pro Gly Lys Ala Ser Val Asn Gln Pro Val
            20                  25                  30

Phe Ala Cys Ser Ala Asn Phe Gln Arg Ile Ser Asp Pro Asn Val Lys
        35                  40                  45

Ser Gly Cys Asp Gly Gly Ser Ala Tyr Ala Cys Ala Asp Gln Thr Pro
    50                  55                  60

Trp Ala Val Asn Asp Asn Phe Ser Tyr Gly Phe Ala Ala Thr Ser Ile
65                  70                  75                  80

Ser Gly Gly Asn Glu Ala Ser Trp Cys Cys Gly Cys Tyr Glu Leu Thr
                85                  90                  95

Phe Thr Ser Gly Pro Val Ala Gly Lys Thr Met Val Val Gln Ser Thr
            100                 105                 110

Ser Thr Gly Gly Asp Leu Gly Thr Asn His Phe Asp Leu Ala Met Pro
        115                 120                 125

Gly Gly Gly Val Gly Ile Phe Asp Gly Cys Ser Pro Gln Phe Gly Gly
    130                 135                 140

Leu Ala Gly Asp Arg Tyr Gly Gly Val Ser Ser Arg Ser Gln Cys Asp
145                 150                 155                 160

Ser Phe Pro Ala Ala Leu Lys Pro Gly Cys Tyr Trp Arg Phe Asp Trp
```

```
                    165                 170                 175
Phe Lys Asn Ala Asp Asn Pro Thr Phe Thr Phe Arg Gln Val Gln Cys
                180                 185                 190

Pro Ser Glu Leu Val Ala Arg Thr Gly Cys Arg Arg Asn Asp Asp Gly
            195                 200                 205

Asn Phe Pro Val Phe Thr Pro Pro Ser Gly Gly Gln Ser Ser Ser Ser
        210                 215                 220

Ser Ser Ser Ser Ser Ala Lys Pro Thr Ser Thr Ser Thr Ser Thr Thr
225                 230                 235                 240

Ser Thr Lys Ala Thr Ser Thr Thr Ser Thr Ala Ser Ser Gln Thr Ser
                245                 250                 255

Ser Ser Thr Gly Gly Gly Cys Ala Ala Gln Arg Trp Ala Gln Cys Gly
            260                 265                 270

Gly Ile Gly Phe Ser Gly Cys Thr Thr Cys Val Ser Gly Thr Thr Cys
        275                 280                 285

Asn Lys Gln Asn Asp Trp Tyr Ser Gln Cys Leu
    290                 295

<210> SEQ ID NO 41
<211> LENGTH: 8
<212> TYPE: PRT
<213> ORGANISM: Staphylotrichum coccosporum IFO 31817
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MUTAGEN
<222> LOCATION: (1)..(1)

<400> SEQUENCE: 41

Gln Ala Asp Gly Lys Ser Thr Arg
1               5

<210> SEQ ID NO 42
<211> LENGTH: 11
<212> TYPE: PRT
<213> ORGANISM: Staphylotrichum coccosporum IFO 31817
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MUTAGEN
<222> LOCATION: (1)..(4)

<400> SEQUENCE: 42

Gln Ser Ala Cys Ala Asp Gly Lys Ser Thr Arg
1               5                   10

<210> SEQ ID NO 43
<211> LENGTH: 21
<212> TYPE: PRT
<213> ORGANISM: Staphylotrichum coccosporum IFO 31817

<400> SEQUENCE: 43

Met Arg Ser Ser Pro Val Leu Arg Thr Ala Leu Ala Ala Leu Pro
1               5                   10                  15

Leu Ala Ala Leu Ala
            20

<210> SEQ ID NO 44
<211> LENGTH: 295
<212> TYPE: PRT
```

<213> ORGANISM: Staphylotrichum coccosporum IFO 31817

<400> SEQUENCE: 44

```
Ala Asp Gly Lys Ser Thr Arg Tyr Trp Asp Cys Cys Lys Pro Ser Cys
1               5                   10                  15
Ser Trp Pro Gly Lys Ala Ser Val Asn Gln Pro Val Phe Ala Cys Ser
            20                  25                  30
Ala Asn Phe Gln Arg Ile Ser Asp Pro Asn Val Lys Ser Gly Cys Asp
        35                  40                  45
Gly Gly Ser Ala Tyr Ala Cys Ala Asp Gln Thr Pro Trp Ala Val Asn
    50                  55                  60
Asp Asn Phe Ser Tyr Gly Phe Ala Ala Thr Ser Ile Ser Gly Gly Asn
65                  70                  75                  80
Glu Ala Ser Trp Cys Cys Gly Cys Tyr Glu Leu Thr Phe Thr Ser Gly
                85                  90                  95
Pro Val Ala Gly Lys Thr Met Val Val Gln Ser Thr Ser Thr Gly Gly
            100                 105                 110
Asp Leu Gly Thr Asn His Phe Asp Leu Ala Met Pro Gly Gly Gly Val
        115                 120                 125
Gly Ile Phe Asp Gly Cys Ser Pro Gln Phe Gly Gly Leu Ala Gly Asp
    130                 135                 140
Arg Tyr Gly Gly Val Ser Ser Arg Ser Gln Cys Asp Ser Phe Pro Ala
145                 150                 155                 160
Ala Leu Lys Pro Gly Cys Tyr Trp Arg Phe Asp Trp Phe Lys Asn Ala
                165                 170                 175
Asp Asn Pro Thr Phe Thr Phe Arg Gln Val Gln Cys Pro Ser Glu Leu
            180                 185                 190
Val Ala Arg Thr Gly Cys Arg Arg Asn Asp Asp Gly Asn Phe Pro Val
        195                 200                 205
Phe Thr Pro Pro Ser Gly Gly Gln Ser Ser Ser Ser Ser Ser Ser Ser
    210                 215                 220
Ser Ala Lys Pro Thr Ser Thr Ser Thr Ser Thr Ser Thr Lys Ala
225                 230                 235                 240
Thr Ser Thr Thr Ser Thr Ala Ser Ser Gln Thr Ser Ser Ser Thr Gly
                245                 250                 255
Gly Gly Cys Ala Ala Gln Arg Trp Ala Gln Cys Gly Gly Ile Gly Phe
            260                 265                 270
Ser Gly Cys Thr Thr Cys Val Ser Gly Thr Thr Cys Asn Lys Gln Asn
        275                 280                 285
Asp Trp Tyr Ser Gln Cys Leu
    290                 295
```

<210> SEQ ID NO 45
<211> LENGTH: 20
<212> TYPE: PRT
<213> ORGANISM: Humicola insolens

<400> SEQUENCE: 45

```
Met Arg Ser Ser Pro Leu Leu Arg Ser Ala Val Val Ala Ala Leu Pro
1               5                   10                  15
Val Leu Ala Leu
            20
```

<210> SEQ ID NO 46
<211> LENGTH: 286
<212> TYPE: PRT
<213> ORGANISM: Humicola insolens

<400> SEQUENCE: 46

```
Ala Ala Asp Gly Lys Ser Thr Arg Tyr Trp Asp Cys Cys Lys Pro Ser
1               5                   10                  15

Cys Gly Trp Ala Lys Lys Ala Pro Val Asn Gln Pro Val Phe Ser Cys
            20                  25                  30

Asn Ala Asn Phe Gln Arg Leu Thr Asp Phe Asp Ala Lys Ser Gly Cys
        35                  40                  45

Glu Pro Gly Gly Val Ala Tyr Ser Cys Ala Asp Gln Thr Pro Trp Ala
    50                  55                  60

Val Asn Asp Asp Phe Ala Phe Gly Phe Ala Ala Thr Ser Ile Ala Gly
65                  70                  75                  80

Ser Asn Glu Ala Gly Trp Cys Cys Ala Cys Tyr Glu Leu Thr Phe Thr
                85                  90                  95

Ser Gly Pro Val Ala Gly Lys Lys Met Val Val Gln Ser Thr Ser Thr
            100                 105                 110

Gly Gly Asp Leu Gly Ser Asn His Phe Asp Leu Asn Ile Pro Gly Gly
        115                 120                 125

Gly Val Gly Ile Phe Asp Gly Cys Thr Pro Gln Phe Gly Gly Leu Pro
    130                 135                 140

Gly Gln Arg Tyr Gly Gly Ile Ser Ser Arg Asn Glu Cys Asp Arg Phe
145                 150                 155                 160

Pro Asp Ala Leu Lys Pro Gly Cys Tyr Trp Arg Phe Asp Trp Phe Lys
                165                 170                 175

Asn Ala Asp Asn Pro Ser Phe Ser Phe Arg Gln Val Gln Cys Pro Ala
            180                 185                 190

Glu Leu Val Ala Arg Thr Gly Cys Arg Arg Asn Asp Asp Gly Asn Phe
        195                 200                 205

Pro Ala Val Gln Ile Pro Ser Ser Ser Thr Ser Ser Pro Val Gly Gln
    210                 215                 220

Pro Thr Ser Thr Ser Thr Thr Ser Thr Ser Thr Ser Ser Pro Pro
225                 230                 235                 240

Val Gln Pro Thr Thr Pro Ser Gly Cys Thr Ala Glu Arg Trp Ala Cys
                245                 250                 255

Gln Cys Gly Gly Asn Gly Trp Ser Gly Cys Thr Thr Cys Val Ala Gly
            260                 265                 270

Ser Thr Cys Thr Lys Ile Asn Asp Trp Tyr His Gln Cys Leu
        275                 280                 285
```

<210> SEQ ID NO 47
<211> LENGTH: 17
<212> TYPE: PRT
<213> ORGANISM: Humicola insolens

<400> SEQUENCE: 47

```
Met Gln Leu Pro Leu Thr Thr Leu Leu Thr Leu Leu Pro Ala Leu Ala
1               5                   10                  15

Ala
```

<210> SEQ ID NO 48
<211> LENGTH: 206
<212> TYPE: PRT
<213> ORGANISM: Humicola insolens

<400> SEQUENCE: 48

```
Ala Gln Ser Gly Ser Gly Arg Thr Thr Arg Tyr Trp Asp Cys Cys Lys
1               5                   10                  15
```

```
Pro Ser Cys Ala Trp Pro Gly Lys Gly Pro Ala Pro Val Arg Thr Cys
            20              25                  30

Asp Arg Trp Asp Asn Pro Leu Phe Asp Gly Gly Asn Thr Arg Ser Gly
            35              40                  45

Cys Asp Ala Gly Gly Ala Tyr Met Cys Ser Asp Gln Ser Pro Trp
    50              55                  60

Ala Val Ser Asp Asp Leu Ala Tyr Gly Trp Ala Ala Val Asn Ile Ala
65              70                  75                      80

Gly Ser Asn Glu Arg Gln Trp Cys Cys Ala Cys Tyr Glu Leu Thr Phe
                85                  90                  95

Thr Ser Gly Pro Val Ala Gly Lys Arg Met Ile Val Gln Ala Ser Asn
                100             105                 110

Thr Gly Gly Asp Leu Gly Asn Asn His Phe Asp Ile Ala Met Pro Gly
            115             120                 125

Gly Gly Val Gly Ile Phe Asn Ala Cys Thr Asp Gln Tyr Gly Ala Pro
        130             135                 140

Pro Asn Gly Trp Gly Gln Arg Tyr Gly Gly Ile Ser Gln Arg His Glu
145             150                 155                 160

Cys Asp Ala Phe Pro Glu Lys Leu Lys Pro Gly Cys Tyr Trp Arg Phe
                165                 170                 175

Asp Trp Phe Leu Asn Ala Asp Asn Pro Ser Val Asn Trp Arg Gln Val
            180                 185                 190

Ser Cys Pro Ala Glu Ile Val Ala Lys Ser Gly Cys Ser Arg
        195                 200                 205
```